(12) United States Patent
Burgess et al.

(10) Patent No.: US 8,202,320 B2
(45) Date of Patent: Jun. 19, 2012

(54) INTERVERTEBRAL DISC PROSTHESIS

(75) Inventors: Ian Burgess, Barrington, RI (US); Matthew Parsons, Dartmouth, MA (US)

(73) Assignee: DePuy Spine, Inc., Rayham, MA (US)

( * ) Notice: Subject to any disclaimer, the term of this patent is extended or adjusted under 35 U.S.C. 154(b) by 1264 days.

(21) Appl. No.: 11/264,522

(22) Filed: Oct. 31, 2005

(65) Prior Publication Data
US 2007/0100454 A1 May 3, 2007

(51) Int. Cl.
*A61F 2/44* (2006.01)
(52) U.S. Cl. .................. 623/17.14; 623/17.15
(58) Field of Classification Search .............. 606/61, 606/246–249; 623/17.11–17.14
See application file for complete search history.

(56) References Cited

U.S. PATENT DOCUMENTS

| | | | |
|---|---|---|---|
| 4,759,766 A | 7/1988 | Buettner-Janz et al. | |
| 5,258,031 A | 11/1993 | Salib et al. | |
| 5,314,477 A | 5/1994 | Marnay | |
| 5,401,269 A | 3/1995 | Büttner-Janz et al. | |
| 5,507,816 A | 4/1996 | Bullivant | |
| 5,556,431 A | 9/1996 | Büttner-Janz | |
| 5,674,296 A | 10/1997 | Bryan et al. | |
| 5,676,701 A | 10/1997 | Yuan et al. | |
| 5,865,846 A | 2/1999 | Bryan et al. | |
| 5,888,226 A | 3/1999 | Rogozinski | |
| 5,899,941 A | 5/1999 | Nishijima et al. | |
| 5,928,284 A | 7/1999 | Mehdizadeh | |
| 6,001,130 A | 12/1999 | Bryan et al. | |
| 6,146,421 A | 11/2000 | Gordon et al. | |
| 6,156,067 A | 12/2000 | Bryan et al. | |
| 6,231,609 B1 | 5/2001 | Mehdizadeh | |
| 6,368,350 B1 | 4/2002 | Erickson et al. | |
| 6,416,551 B1 | 7/2002 | Keller | |
| 6,419,706 B1 | 7/2002 | Graf | |
| 6,517,580 B1 | 2/2003 | Ramadan et al. | |
| 6,607,558 B2 | 8/2003 | Kuras | |
| 6,645,248 B2 | 11/2003 | Casutt | |
| 6,682,562 B2 * | 1/2004 | Viart et al. .................. | 623/17.14 |
| 6,706,068 B2 * | 3/2004 | Ferree ......................... | 623/17.11 |
| 2003/0074076 A1 * | 4/2003 | Ferree et al. ................ | 623/17.16 |
| 2003/0220649 A1 | 11/2003 | Bao et al. | |
| 2003/0220691 A1 | 11/2003 | Songer et al. | |
| 2004/0002761 A1 | 1/2004 | Rogers et al. | |
| 2004/0054411 A1 | 3/2004 | Kelly et al. | |
| 2004/0073307 A1 | 4/2004 | Keller | |
| 2004/0073311 A1 | 4/2004 | Ferree | |
| 2004/0073312 A1 | 4/2004 | Eisermann et al. | |
| 2004/0073313 A1 * | 4/2004 | Link et al. .................. | 623/17.15 |
| 2004/0260396 A1 | 12/2004 | Ferree et al. | |
| 2005/0043804 A1 * | 2/2005 | Gordon et al. ............. | 623/17.16 |

OTHER PUBLICATIONS

Johnson & Johnson: DepuySpine™: Charité™ Centreline™ TDR Instrumentation: *Surgical Technique* (20 pages).

* cited by examiner

*Primary Examiner* — Eduardo C Robert
*Assistant Examiner* — Tara Carter

(57) ABSTRACT

A method of implanting an intervertebral disc prosthesis in a patient comprises selecting a superior and inferior endplates from a plurality of endplates having different endplate features. The different endplate features include different structural and material composition features. In addition, a core is selected from a plurality of cores having different core features such as different structural and material composition features. In one embodiment, the core is a composite core comprised of a first material and a different second material. After the endplates and core are selected, the intervertebral disc prosthesis is assembled with the selected core positioned between the selected endplates. The assembled intervertebral disc prosthesis is then positioned on an insertion tool and implanted in the patient.

18 Claims, 19 Drawing Sheets

INTERVERTEBRAL DISC PROSTHESIS

BACKGROUND

This invention relates to the field of prosthetics, and more particularly, to an intervertebral disc prosthesis designed to replace a damaged intervertebral disc.

The human spine consists of twenty-four small bones known as vertebrae, or "vertebral bodies," that protect the spinal cord and provide stability to the torso. The vertebrae are arranged in a column and stacked vertically upon each other. Between each vertebra is a fibrous bundle of tissue called an intervertebral disc. These intervertebral discs act as a cushion to the spinal column by absorbing energy and transmitting loads associated with everyday movement. They also prevent the vertebrae from rubbing against each other.

Each intervertebral disc comprises two distinct regions. A firm outer region, the annulus, maintains the shape of the intervertebral disc. An inner region, the nucleus, provides a resilient tissue that enables the disc to function as a shock absorber. Over time, the normal aging process causes the intervertebral discs to degenerate, diminishing their water content and thereby reducing their ability to properly absorb the impact associated with spinal movements. Diminished water content in the intervertebral discs may also cause the vertebrae to move closer together. Tears and scar tissue can weaken the discs, resulting in injury. When the discs wear out or are otherwise injured, a condition known as degenerative disc disease results. With this condition, discs do not function normally and may cause pain and limit activity.

The condition of degenerative disc disease can potentially be relieved by a surgical procedure called artificial disc replacement. In this procedure, the damaged intervertebral disc is replaced by a prosthetic disc. One well known intervertebral prosthetic disc is produced by DePuy Spine, Inc. of Raynaham, Mass. and is sold under the trademark CHARITÉ®. This disc prosthesis is comprised of two metal endplates and a center polyethylene core. The center core includes a superior spherical bearing surface and an inferior spherical bearing surface. The superior endplate includes a concave surface that fits upon and is congruent with the superior bearing surface of the core. The inferior endplate includes a concave surface that fits under and is congruent with the inferior bearing surface of the core. During the CHARITÉ® artificial disc replacement procedure, the damaged disc is first removed via an anterior surgical approach and the end surfaces of the exposed vertebrae are cleared of debris. The vertebrae are spread apart and the metal endplates are positioned on the respective vertebra and tapped into place. The polyethylene core is then inserted between the endplates and the vertebrae are returned to their normal position. The pressure of the spinal column further seats the endplates into the vertebral bones and secures the core in place.

Although current intervertebral disc prosthetic devices have enjoyed success, it would be beneficial to add additional desirable features to the prosthetic device. For example, it would be desirable to design the prosthetic device to more closely mimic the true anatomy and physiology of an intact intervertebral disc. Additionally, it would be advantageous to allow for alternate means of fixation of the implant to the surrounding bone. Furthermore, the implant could be improved by designing an instrument interface that is more compact, enhances ease of insertion, and accommodates non-anterior surgical approaches and/or revision procedures. For example, it would be desirable to provide feature that would allow the intervertebral disc prosthesis to be implanted in the patient as a unitary assembled piece rather than sequential component-by-component implantation. In addition, it would be advantageous to design the intervertebral disc prosthesis such that the implant materials and core geometry are modular, and can be selected to suit specific patient and/or surgeon needs. For example, for a patient with nickel hypersensitivity, non-sensitizing implant materials could be selected. Similarly, for surgeons that desire MRI compatibility, non-ferromagnetic materials could be selected.

SUMMARY

An intervertebral disc prosthesis comprises a first plate, a second plate, and a core sandwiched between the first plate and the second plate. The first plate and second plate both include a socket, an anterior edge and a posterior edge. The core includes two substantially spherical articular surfaces, including a first articular surface engaging the first socket and a second articular surface engaging the second socket.

In one embodiment, the core is comprised of at least two portions, each of which is comprised of a different material. For example, the substantially spherical articular surfaces of the core could be formed from a relatively soft material, and the radial flange around the core could be formed from a relatively hard material. In this manner, a composite core is provided with material properties that vary throughout the geometry of the component.

In one embodiment, the second plate is either prohibited or substantially restricted from rotating on the prosthesis core. To this end, the core includes a radial flange that extends to the second endplate and encompasses the second socket, thereby preventing movement of the core in the second socket, while allowing movement of the core in the first socket.

In another embodiment, the first plate of the intervertebral disc prosthesis may be comprised of an MRI compatible material such as titanium. Furthermore, the endplates and core may be comprised of various materials that provide preferred wear characteristics or provide non-sensitizing options for potentially hyper-sensitive (e.g., nickel sensitive) patients.

Also disclosed herein is a method of assembling an intervertebral disc prosthesis for implantation in a patient is disclosed herein. The method comprises determining at least one desired feature of the intervertebral disc prosthesis based on the individual circumstances of the patient. After a desired feature of the intervertebral disc prosthesis is selected, the components of the intervertebral disc prosthesis are selected. In particular, a superior endplate is selected from a plurality of superior endplates having different structural and material composition features. In addition, an inferior endplate is selected from a plurality of inferior endplates having different structural and material composition features. Furthermore, a core is selected from a plurality of cores having different structural and material composition features. The selected superior endplate, inferior endplate and core are all selected core selected based on the at least one desired feature of the intervertebral disc prosthesis. After the components are selected, the intervertebral disc prosthesis is assembled into a unitary piece. The selected core is positioned between the superior endplate and the inferior endplate.

A method is also disclosed for providing intervertebral disc prostheses to physicians for implantation in different patients. The method comprises making a plurality of modular endplates and a plurality of modular cores available to the physicians for selection. The plurality of modular endplates and the plurality of modular cores have different features such as different structural and material composition features. Although the plurality of modular endplates and the plurality of modular cores have different features, each of the plurality of modular endplates is configured to engage any one of the plurality of modular cores. Orders are received for various intervertebral disc prostheses, wherein each of the received orders specifies at least one of the plurality of modular endplates and at least one of the plurality of modular cores. The specified endplates and core for a given intervertebral disc prosthesis are chosen by the physician based on the facts concerning a particular patient. After the endplates and core are ordered, the components are sent to the physician for assembly and implantation in the patient.

A method of implanting an intervertebral disc prosthesis in a patient is also disclosed herein. The method comprises selecting a superior endplate from a plurality of superior endplates having different superior endplate features such as different structural and material composition features. An inferior endplate is also from a plurality of inferior endplates having different inferior endplate features. In addition, a core is selected from a plurality of cores having different core features such as different structural and material composition features. After the endplates and core are chosen, the intervertebral disc prosthesis is assembled with the selected core positioned between the selected superior endplate and the selected inferior endplate. The assembled intervertebral disc prosthesis is then positioned on an insertion tool and implanted in the patient.

DESCRIPTION

General Structure

Figure 1:
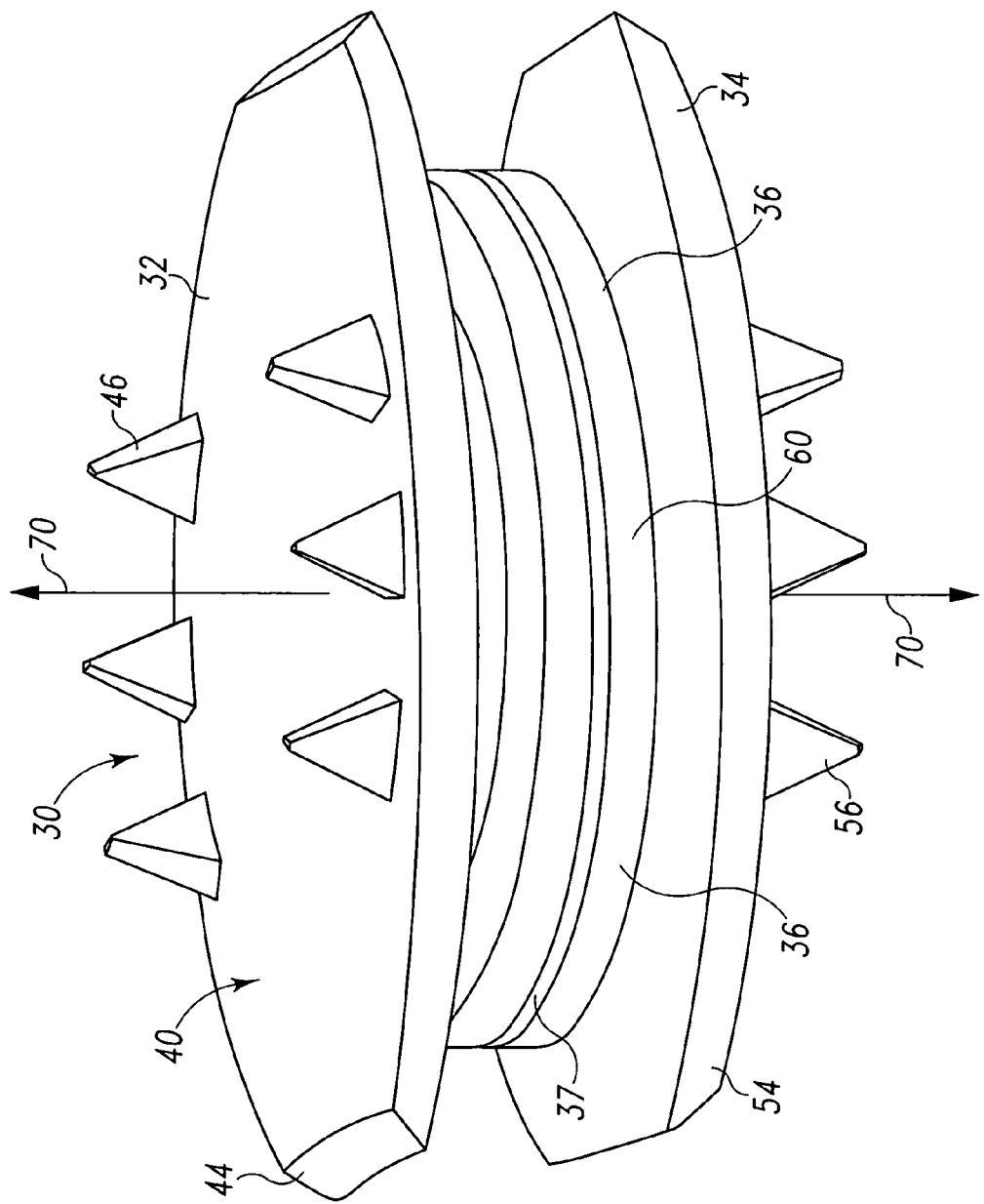
FIG. 1 shows an superior perspective view of an intervertebral disc prosthesis including a superior plate and a inferior plate separated by a core.
Figure 2:
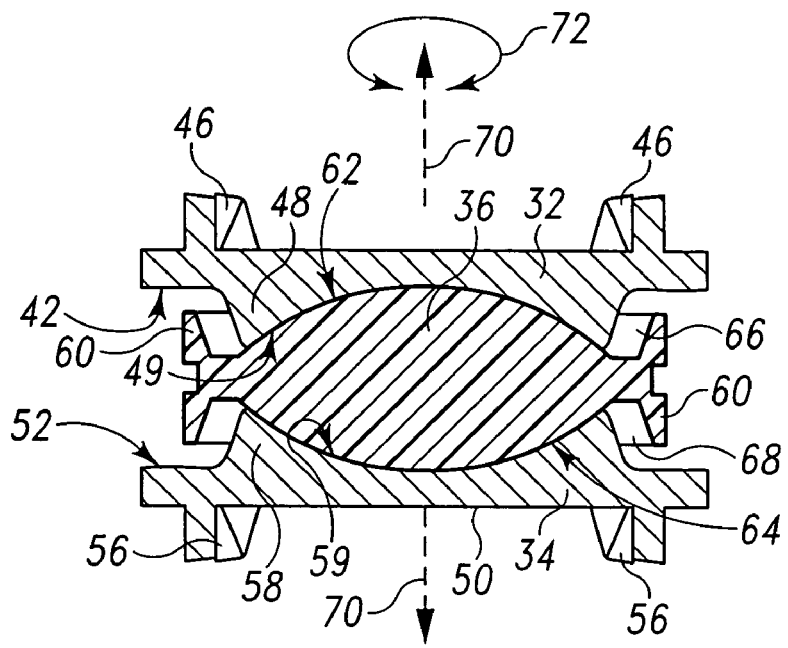
FIG. 2 shows a side cross-sectional view of the intervertebral disc prosthesis of FIG. 1.
Figure 3:
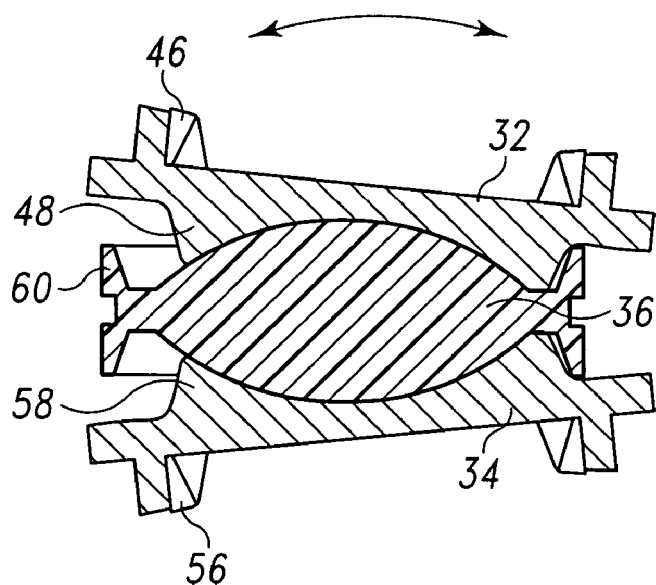
FIG. 3 shows a side cross-sectional view of the intervertebral disc prosthesis of FIG. 1 with the superior plate rotated to display flexion.

With reference to FIGS. 1-3, an intervertebral disc prosthesis 30 comprises a superior plate 32, an inferior plate 34, and a core 36. The core 36 is sandwiched between the superior plate 32 and the inferior plate 34. The superior plate 32 and the inferior plate 34 ride upon the core 36 and are operable to rotate relative to the core.

The superior plate 32 serves as a first endplate for the prosthetic device 30. In one embodiment, the superior plate 32 is comprised of metal. In particular, the superior plate 32 may be comprised of a medical grade cobalt chromium alloy. The superior plate 32 comprises an upper surface 40 on one side and a lower surface 42 on the other side. An outer perimeter edge 44 defines the "footprint" shape of the superior plate 32.

The upper surface 40 of the superior plate 32 is designed for engagement with a vertebral surface of a patient. To this end, the upper surface 40 of the superior plate may be slightly convex for close engagement with the slightly concave vertebral surface of the patient. A typical convexity of the superior plate is based on a 90-200 mm radius of curvature. The preferred convexity will vary from patient to patient, depending upon the size and vertebral surface shape of the patient.

Teeth 46 are included on the upper surface 40 of the superior plate 32. The teeth 46 are designed to penetrate into the vertebral surface, helping to secure the superior plate 32 to the vertebral surface. As explained in further detail below, certain advantages are achieved based on the positioning of the teeth on the plate 32, the size of the teeth 46, and the shape of the teeth. Screws (not shown) may also be threaded through holes (not shown) in the superior plate to provide further assistance in securing the superior plate 32 to the vertebral surface.

The inferior surface 42 of the superior plate 32 is generally flat near the outer perimeter edge 44. However, with reference to FIGS. 2-3, a donut-shaped collar portion 48 depends from the center of the inferior surface 42 of the plate 32. An inner concave surface 49 is provided at the center of the collar portion 48. As explained in further detail below, this inner concave surface 49 serves as a socket for a ball and socket arrangement.

The inferior plate 34 is a mirror image of the superior plate 32 and is also made of a medical grade cobalt chromium alloy. The inferior plate 34 includes a slightly convex inferior surface 50 outlined by an outer perimeter edge 54. A plurality of teeth 56 extend from the inferior surface 50. The teeth 56 are designed to help secure the inferior plate 34 to a vertebral surface. The upper surface 52 of the inferior plate 34 includes a collar portion 58 with an inner concave surface 59 which provides a socket for the core.

The prosthesis core 36 is sandwiched between the superior plate 32 and the inferior plate 34. The core 36 is arranged within an interior space of the prosthesis 30 defined between the lower surface 42 of the superior plate 32 and the upper surface 52 of the inferior plate 34. In one embodiment, the prosthesis core 36 is comprised of a plastic material having a high resistance to wear, such as ultra high molecular weight polyethylene (UHMWPE), which allows the endplates 32 and 34 to slide easily on the core. The prosthesis core 36 is generally disc shaped with an outer radial flange 60, an upper spherical surface 62, and a lower spherical surface 64. As shown in FIG. 2, a first groove 66 is formed between the flange 60 and the superior spherical surface 62. A second groove 68 is formed between the flange 60 and the inferior spherical surface 64.

When the prosthesis 30 is assembled, the concave surface 49 of the superior plate 32 and the upper spherical surface 62 of the core 36 engage one another and form articular surfaces. Likewise, the concave surface 59 of the inferior plate 34 and the lower spherical surface 64 of the core 36 engage one another and form articular surfaces.

In one preferred embodiment, the articular surfaces 49, 62, 59, 64 are spherical and remain congruous during torsional rotation around the vertical axis 70. In this embodiment, the radii of the arcs in the frontal (lateral bending) planes equal to the radii of the arcs in the sagittal (flexion) planes. This allows the plates 32 and 34 to rotate upon the core 36, including rotation in the transversal plane (torsion) while the articular surfaces remain in congruous contact. In this embodiment, the articular surfaces 49, 62, 59, 64 do not offer significant resistance to torsional rotation.

With reference to FIG. 3, the radial flange 60 and associated grooves 66 and 68 provide for limited movement of the endplates in the frontal (lateral bending) plane and sagittal (flexion/extension) plane. In particular, at a certain angle of rotation of the superior plate 32 relative to the inferior plate 34 in the frontal and sagittal planes, the flange 60 of the prosthesis core engages the collar portions 48 and 58 of the endplates 32, 34. This provides a defined stop against excessive rotation in the frontal (lateral bending) plane and sagittal (flexion/extension) plane of the prosthesis 30.

Further Embodiments

Figure 4:
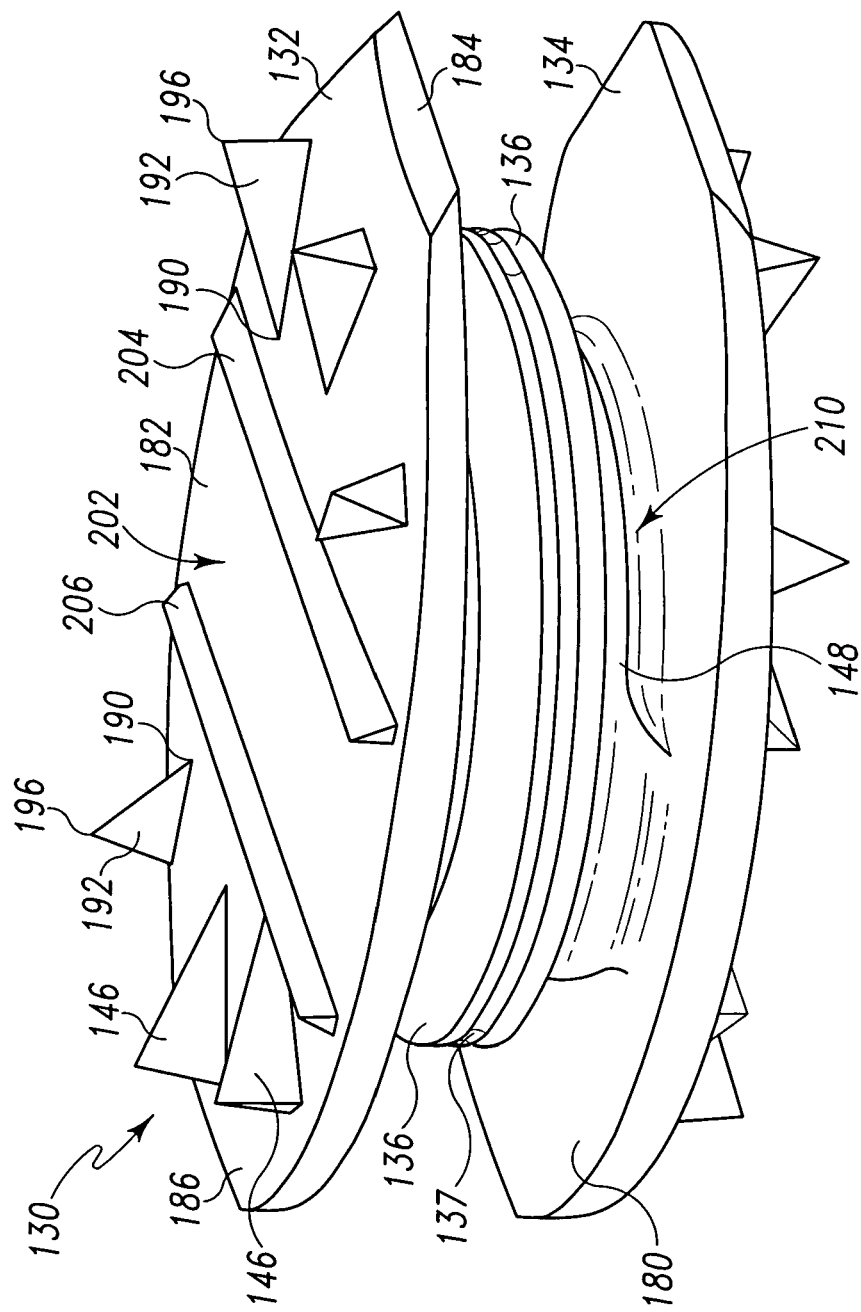
FIG. 4 shows a perspective view of an alternative embodiment of the intervertebral disc prosthesis of FIG. 1.

With reference to FIG. 4, an alternative embodiment of an intervertebral disc prosthesis 130 is shown. As shown in FIG. 4, the prosthesis 130 comprises a superior plate 132, an inferior plate 134 and a core 136 sandwiched between the superior plate 132 and the inferior plate 134. The superior plate 132 is generally symmetric to the inferior plate 134. The plates are configured to include an anterior side 180, a posterior side 182, a left side 184, and a right side 186.

Figure 10:
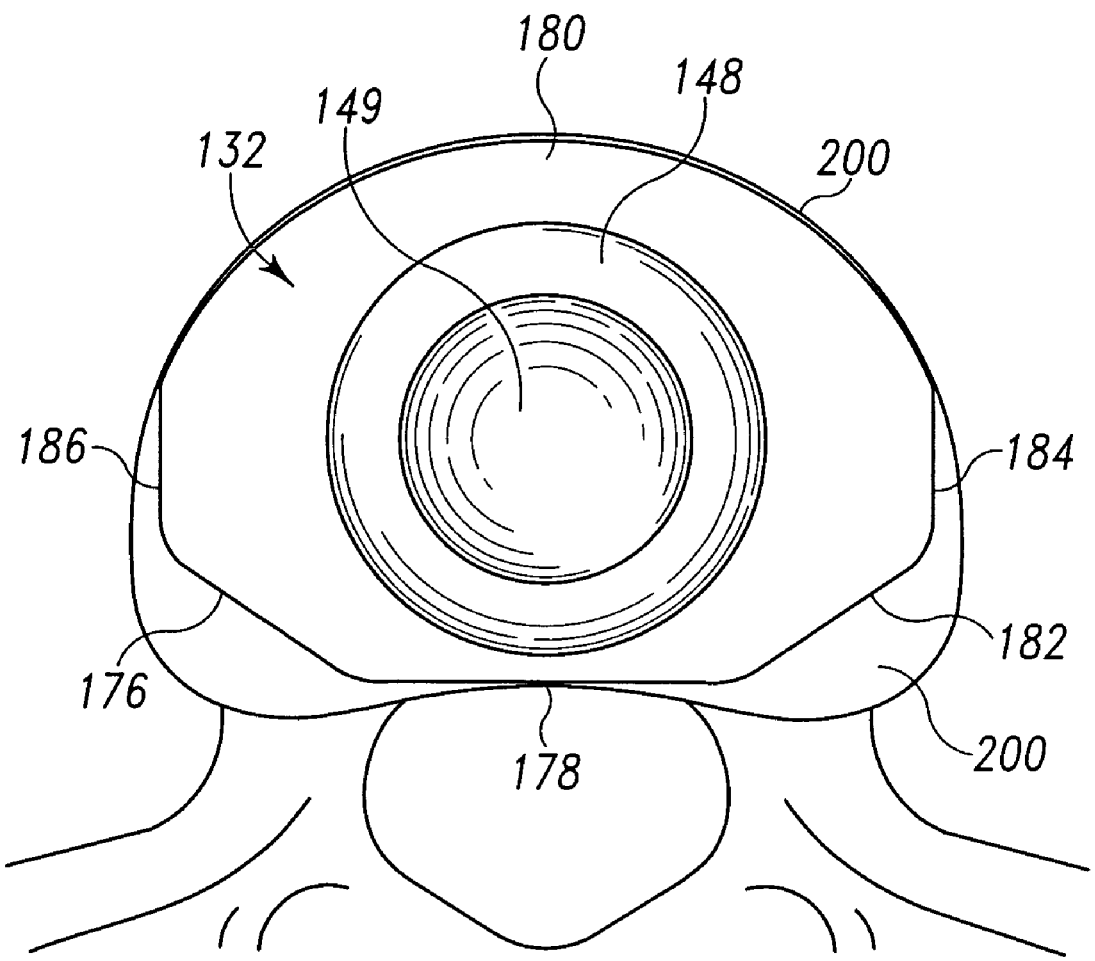
FIG. 10 shows a bottom plan view of the superior plate of FIG. 6 and its footprint in relation to a vertebral body.

The "footprint" of each endplate 132 and 134 is designed to provide a more anatomically representative endplate shape that generally conforms to the vertebral endplate anatomy, as shown in FIG. 10. The left side 184 of the superior endplate 132 is generally flat and parallel to the right side 186 of the plate 132. The anterior side 180 of the endplate 132 is generally arched and provides a curved edge that extends from the left side 184 to the right side 186 of the endplate 132. The posterior side 182 of the endplate includes three angled edges that give the endplate a trapezoidal appearance. In particular, the posterior side 182 of the endplate 132 includes a rear edge 178, a left bevel 174 joining the rear edge 178 to the left edge 184, and a right bevel 176 joining the rear edge 178 to the right edge 186. As shown in FIG. 10, the above-described endplate footprint allows the endplate to substantially conform to the vertebral body 200 of the patient. In particular, the endplate footprint covers a substantial portion of the vertebral body, thus providing additional surface area for connection and bony in-growth between the endplate and the vertebral body. This in-growth may be facilitated by a porous bony in-growth coating on the endplates.

In addition to the above, each endplate 132 and 134 of the prosthesis 130 is slightly convex for close engagement with the slightly concave vertebral surface of the patient. A typical convexity of the superior plate is based on a 90-200 mm radius of curvature. The preferred convexity will vary from patient to patient, depending upon the patient's size and vertebral surface shape.

Endplate Teeth and Fixation Features

Figure 5:
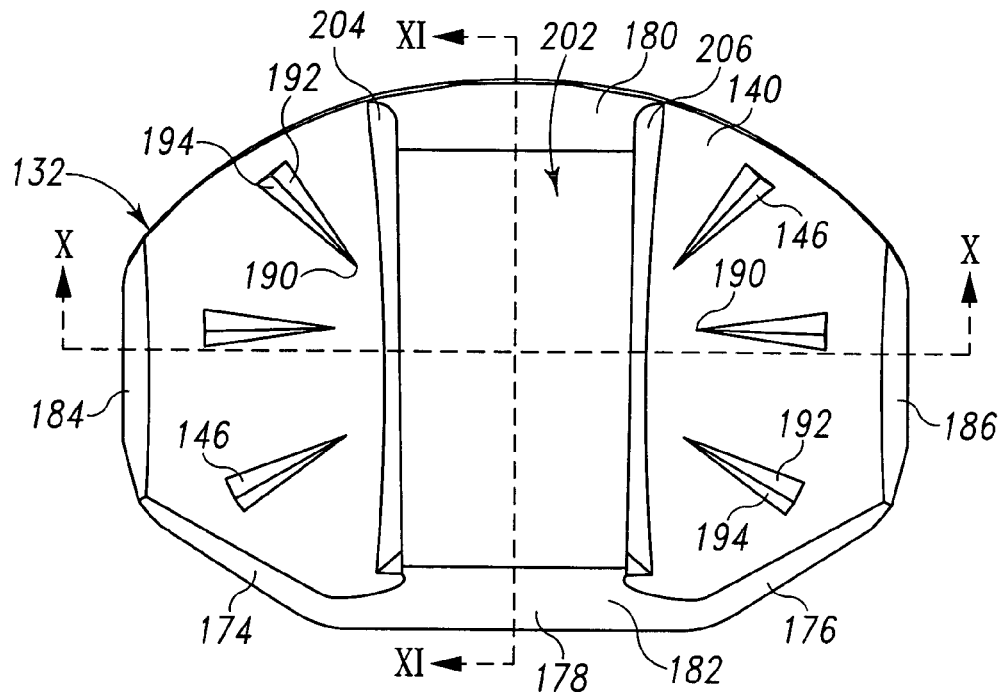
FIG. 5 shows a top plan view of the intervertebral disc prosthesis of FIG. 4 including a top plan view of a superior plate of the intervertebral disc prosthesis.

As shown in FIGS. 4 and 5, the teeth 146 of the endplates 132 and 134 are generally pyramidal in shape with a triangular base positioned on the outer surface 140 of the endplate (i.e., the upper surface of the superior endplate). The triangular base is an acute triangle with two of the triangular sides significantly longer than the triangular side opposite the vertex 190 of the triangular base. This results in pyramidal shaped teeth having two elongated faces 192, 194. The teeth are arranged radially upon the endplates 132 and 134 with the vertex 190 of each triangular base pointed toward a central portion of the endplate. The teeth 146 are also generally positioned toward the left side 184 and right side 186 of the endplates. The radial arrangement of the teeth 146 on the left and right sides of the endplate results in the elongated faces 192 and 194 of the teeth directed generally toward the anterior or posterior sides of the endplates (i.e., anterior-posterior faces).

Each pyramidal shaped tooth 146 may be further defined by a width and a height. The width of the tooth 146 is generally defined as the distance between the vertex 190 of the triangular base and the opposing side of the triangular base on the surface of the endplate. The height of the tooth is generally defined as the perpendicular distance from the pyramidal vertex 196 of the tooth 146 to the face of the endplate. The teeth shown in FIGS. 4 and 5 are broad teeth having a width that is greater than their height. This generally short yet broad tooth structure allows the prosthesis 130 to be more easily inserted into the intervertebral space than those prosthetic devices with longer teeth. This tooth structure also results in broad antero-posterior faces. The broad antero-posterior faces provide significant resistance to migration and antero-posterior shear/expulsion once the prosthetic device is in place in the intervertebral space. The radial arrangement of the teeth provides resistance to lateral shear and rotation relative to the vertebral bodies.

Figure 13:
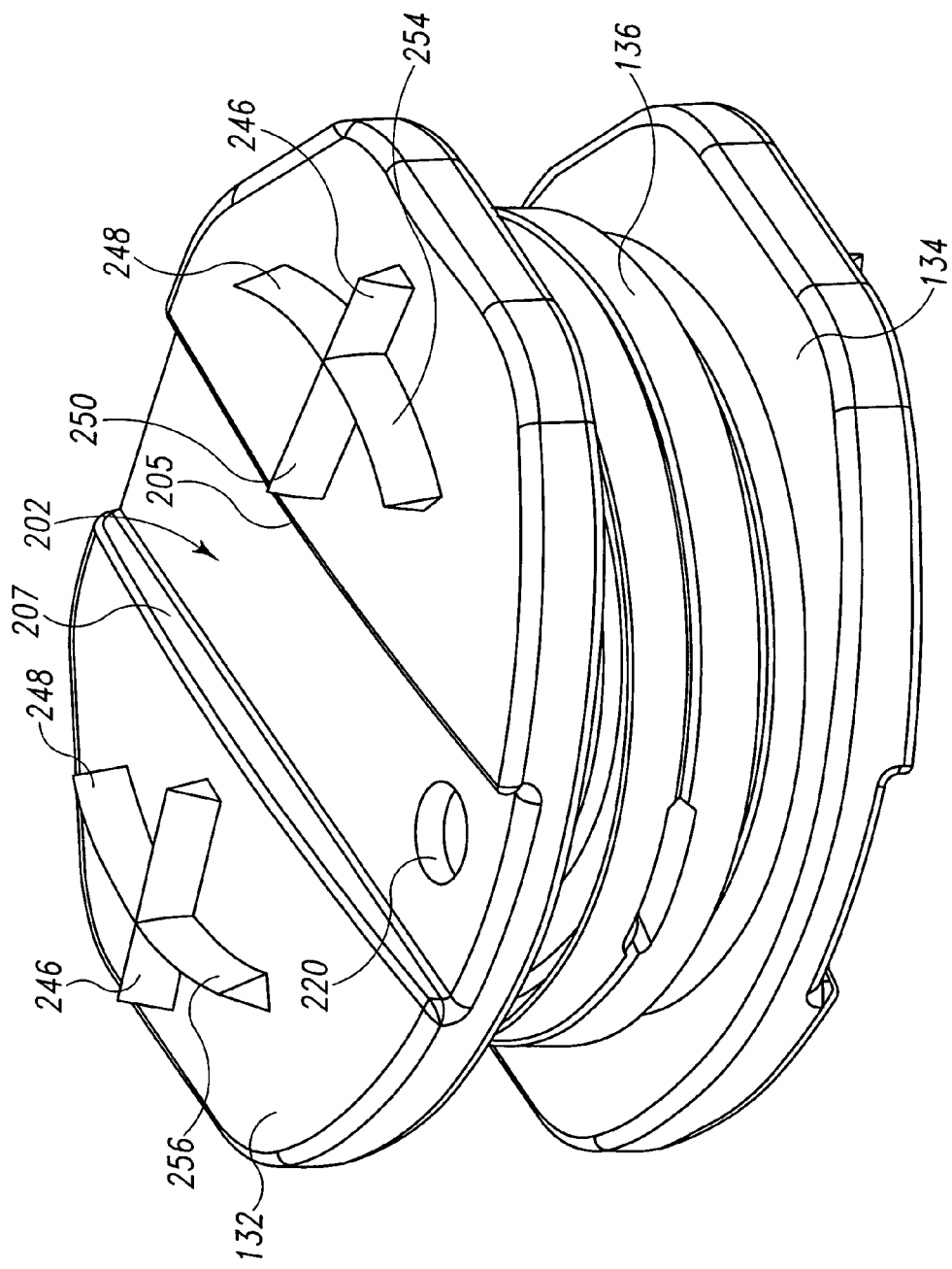
FIG. 13 shows a perspective view of an alternative embodiment of the intervertebral disc prosthesis of FIG. 4.

Another alternative embodiment of the teeth is shown in FIG. 13. The teeth of FIG. 13 include two elongated radial teeth 246 and two elongated circumferential teeth 248. The radial teeth are wedge shaped and extend laterally from right to left near the lateral midline of the prosthesis. Each radial tooth includes an elongated anterior face 250 and an elongated posterior face (not shown). The circumferential teeth 248 bisect the radial teeth 246 as they extend circumferentially upon the face of the endplate. The circumferential teeth 248 are also wedge shaped. Each circumferential tooth 248 includes an exterior face 254 and an interior face 256. Together, the radial teeth 246 and circumferential teeth 248 form cross-shaped teeth on the left side and the right side of each endplate face. The teeth are relatively short and broad, allowing the intervertebral prosthesis to be more easily inserted in the intervertebral space. In addition, the cross-shaped tooth arrangement is configured to provide significant resistance to migration of the endplates once the intervertebral prosthesis is positioned in a patient.

In addition to the above features, in one embodiment the teeth further comprise pockets, slots or other texture on the surfaces of the teeth, such as the antero-posterior faces 192 and 194. Bone morphogenetic protein (BMP), bone marrow, Healos®, or other bone graft substitute or catalyst, or combinations thereof, may be packed or coated on the textured surfaces of the teeth to promote bony in-growth and attachment between the endplate and bone.

In addition to textured surfaces on the teeth, textured surfaces may also be provided on other portions of the face of the endplate. For example, as shown in FIG. 11A, the face 140 of the endplate 132 includes a textured portion 147. The textured portion 147 is coated with a material that is doped with osteoinductive substances. In one embodiment, the coating includes a carrier used to deliver a timed release of osteoinductive substances. These substances promote attachment of bone to the endplates. For example, in one embodiment, the coating includes a resorbable portion such as calcium phosphate, hydroxyapatite, collagen, mineralized collagen, PGA, PLA, hydrogels or combinations thereof. The resorbable portion is impregnated with an osteoinductive substance, such as BMP, the patient's bone marrow, stem cell concentrates, or combinations thereof. As the resorbable component breaks down in the body, the osteoinductive substance is released and promotes bony ingrowth/attachment to the non-resorbable portion of the coating, such as titanium, metal matrix composite (MMC), ceramic or combinations thereof.

Posterior Center of Rotation

Figure 6:
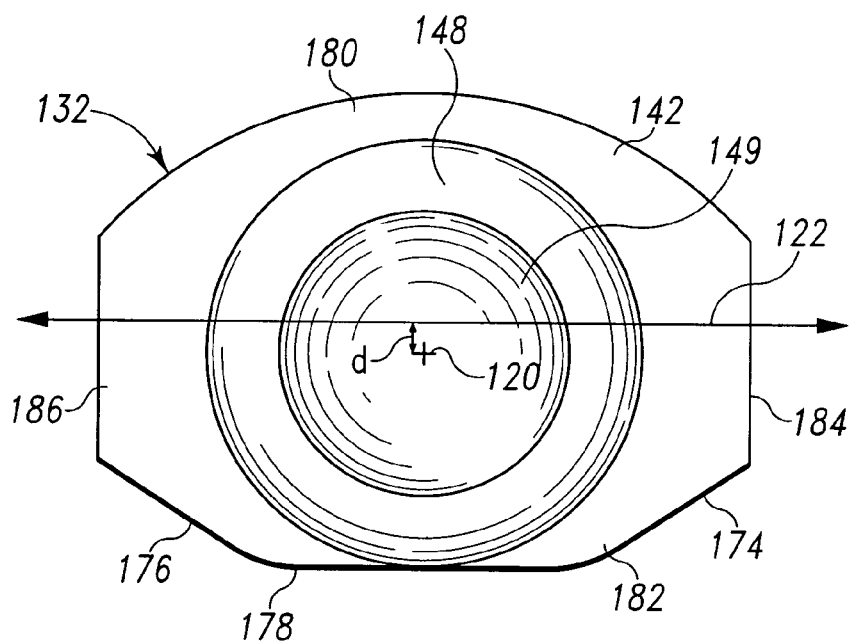
FIG. 6 shows a bottom plan view of the superior plate of the intervertebral disc prosthesis of FIG. 5, showing an articulation socket.

FIG. 6 shows a plan view of the lower surface 142 of the superior plate 132 of one embodiment of the intervertebral disc prosthesis 130. As shown in FIG. 6, a donut-shaped collar portion 148 is included on the lower surface 142 of the upper plate 132. The collar 148 extends outward from other portions of the lower surface 142 and surrounds a semi-spherical concave surface 149 that provides a socket for the core 136 of the prosthesis. The concave surface 149 defines a center-of-rotation for the superior plate 132 relative to the core 136. The position of the center of rotation is shown in FIG. 6 by a "+" 120. Also shown in FIG. 6 is a lateral midline 122 extending laterally across the plate from the left side 184 to the right side 186. The lateral midline 122 is a line located directly between the furthermost anterior edge and the furthermost posterior edge of the endplate 132.

As shown in FIG. 6, the radial collar 148 is centered upon the plate such that it is closer to the posterior edge 182 than the anterior edge 180 of the plate. As a result, the center of rotation 120 of the superior plate 132 is positioned to the posterior of the lateral midline 122. In particular, the center of rotation 120 is located a distance "d" behind the lateral midline 122. In a preferred embodiment, the center of rotation is 1 mm to 3 mm posterior to the lateral midline. This posterior center of rotation arrangement closely mimics the true anatomy of healthy vertebral bodies and intervertebral discs.

Insertion Features

Figure 7:
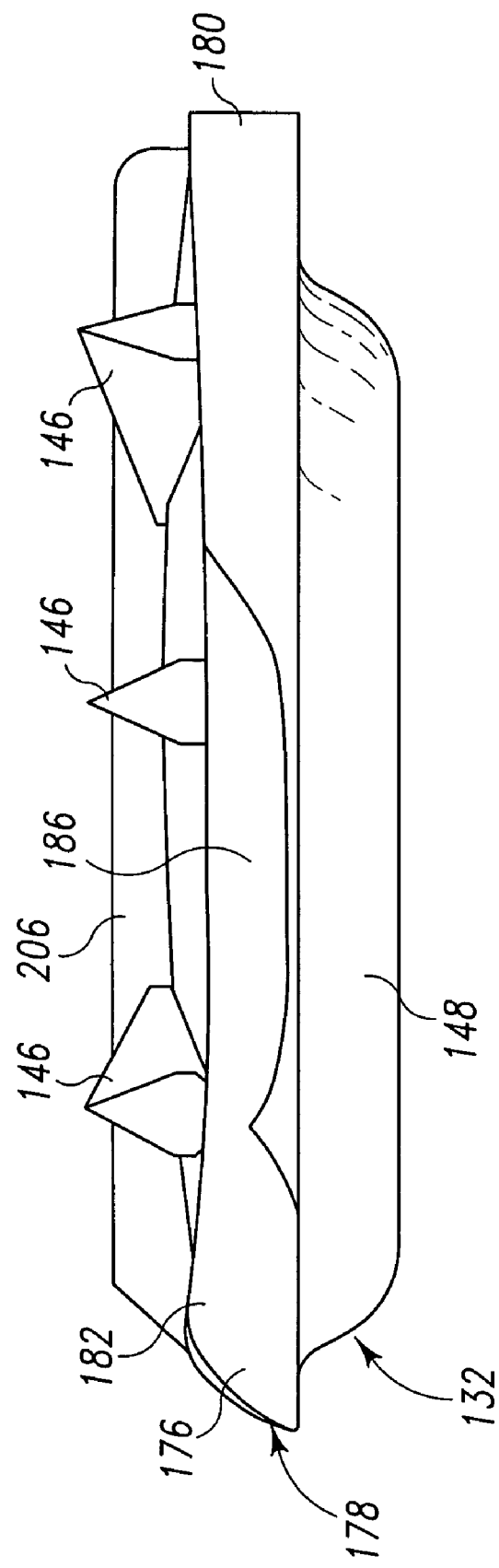
FIG. 7 shows a right side elevational view of the superior plate of the intervertebral disc prosthesis of FIG. 5.

With continued reference to FIGS. 4-7, the endplates 132 and 134 of the prosthesis are designed with several features that allow the prosthesis 130 to be more easily inserted into the intervertebral space. For example, as best seen in FIG. 7, the posterior side 182 of the endplate 132 is bulleted such that the rear edge 176, left bevel 174, and right bevel 176 are all tapered and provide a generally pointed edge. This tapered edge on the posterior side 182 of endplate allows the endplate to be more easily inserted into a collapsed intervertebral space if an anterior approach is taken when inserting the prosthesis 130. In particular, the tapered rear edge 176 provides a bulleted surface to help wedge the prosthesis in the intervertebral space. In addition, the left edge 184 and right edge 186 are tapered. These tapered edges further allow the endplate to be more easily inserted into a collapsed intervertebral space if a lateral approach is taken when inserting the prosthesis 130.

While the posterior side 182 of the prosthesis 130 is tapered, the anterior side 180 is more flat and blunt. As explained in further detail below, this blunt side 180 provides a flat anterior surface that may be pressed upon as the endplate is forced into the intervertebral space during insertion from an anterior approach.

In addition to the above, the prosthesis 130 includes a central channel/slot 202 formed on the face of the superior plate 132, as shown in FIGS. 4 and 5. The central channel 202 is formed by a left side rail 204 and a right side rail 206 that extend above the face of the superior plate from the anterior side 180 to the posterior side 182 and define the sides of the central channel 202. As explained in further detail below, the central channel is designed to engage a distracting ramp provided by an insertion arm of on an disc insertion tool, thus facilitating insertion of the prosthesis device into the intervertebral disc space.

In one alternative embodiment, the central channel 202 may be defined by oblique rails or lateral rails that extend across the face of the superior plate 130 at 45° or 90° angles with respect to the rails 204 and 206 shown in FIGS. 4 and 5. Such oblique rails or lateral rails would facilitate oblique or lateral insertion of the intervertebral disc prosthesis 130.

Figure 11:
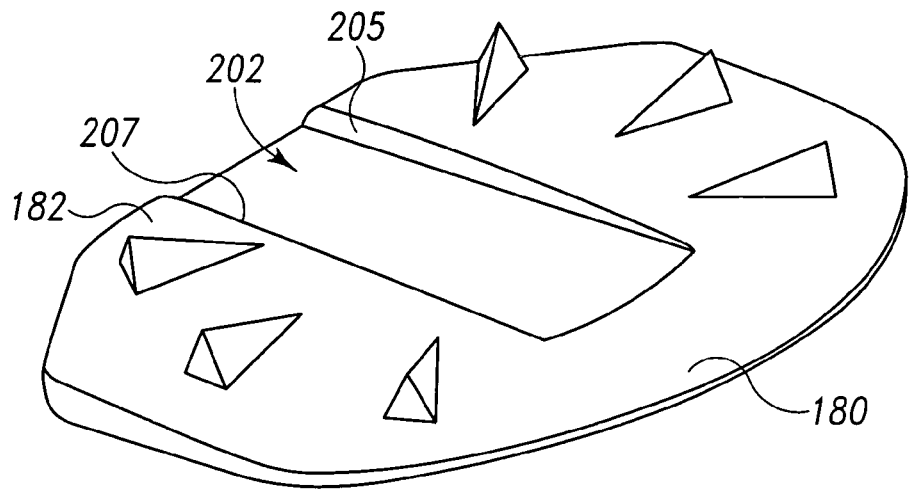
FIG. 11 shows a perspective view of an alternative embodiment of an endplate of the intervertebral disc prosthesis of FIG. 4.
Figure 11A:
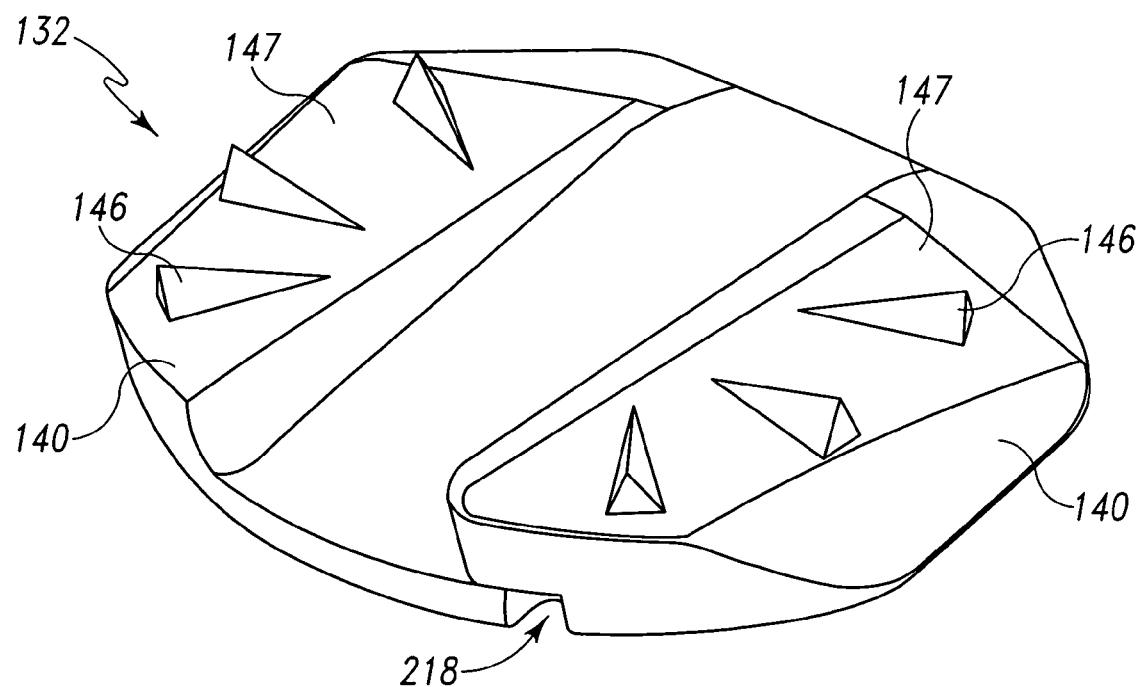
FIG. 11A shows a perspective view of another alternative embodiment of the endplate of FIG. 11 including a coating on the face of the endplate.

In yet another alternative embodiment, the central channel may be embedded in the face of the endplate, such as that shown in FIG. 11. In this embodiment, the central channel 202 is defined by a left side rail embedded in the face of the plate to form a left side wall 205. Likewise the right side rail is embedded in the face such that it forms a right side wall 207. The central channel 202 gradually ramps deeper into the face of the endplate from the anterior to the posterior. In this embodiment, the endplate itself becomes gradually thicker from the anterior side 180 to the posterior side 182 of the endplate. This allows the endplate to incorporate a lordotic angle in the sagittal plane of the prosthesis. For example, if each endplate incorporates a 3.5° angle from anterior to posterior, the intervertebral prosthesis as a whole will incorporate a 7° lordotic angle in the sagittal plane. Endplates incorporating such a lordotic angle may desirable for certain patients.

Figure 8:
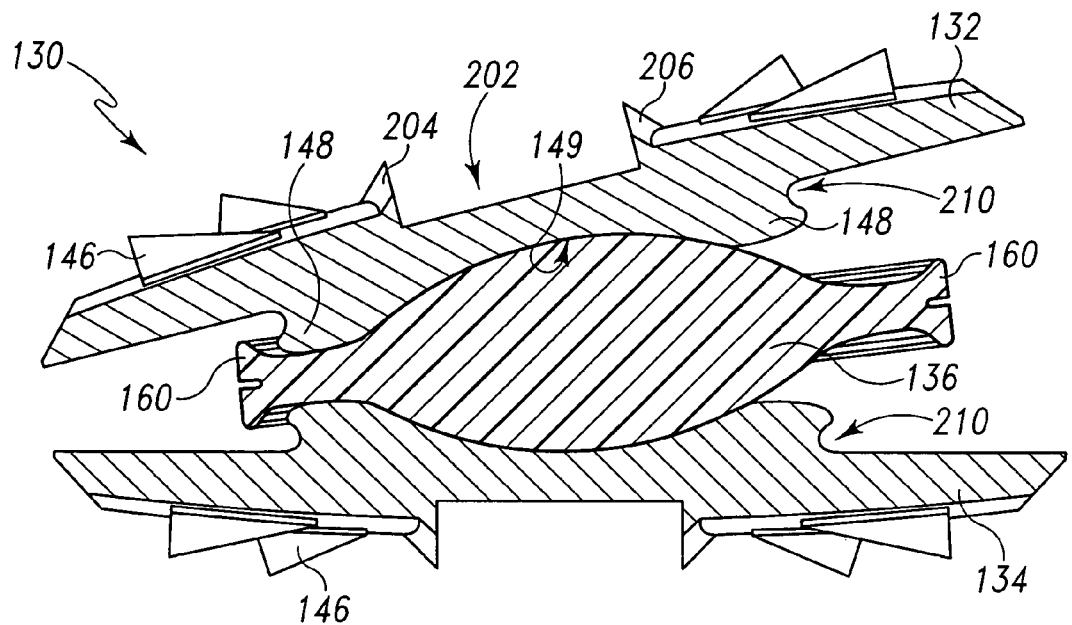
FIG. 8 shows a cross-sectional view of the intervertebral disc prosthesis through line X-X of FIG. 5.
Figure 9:
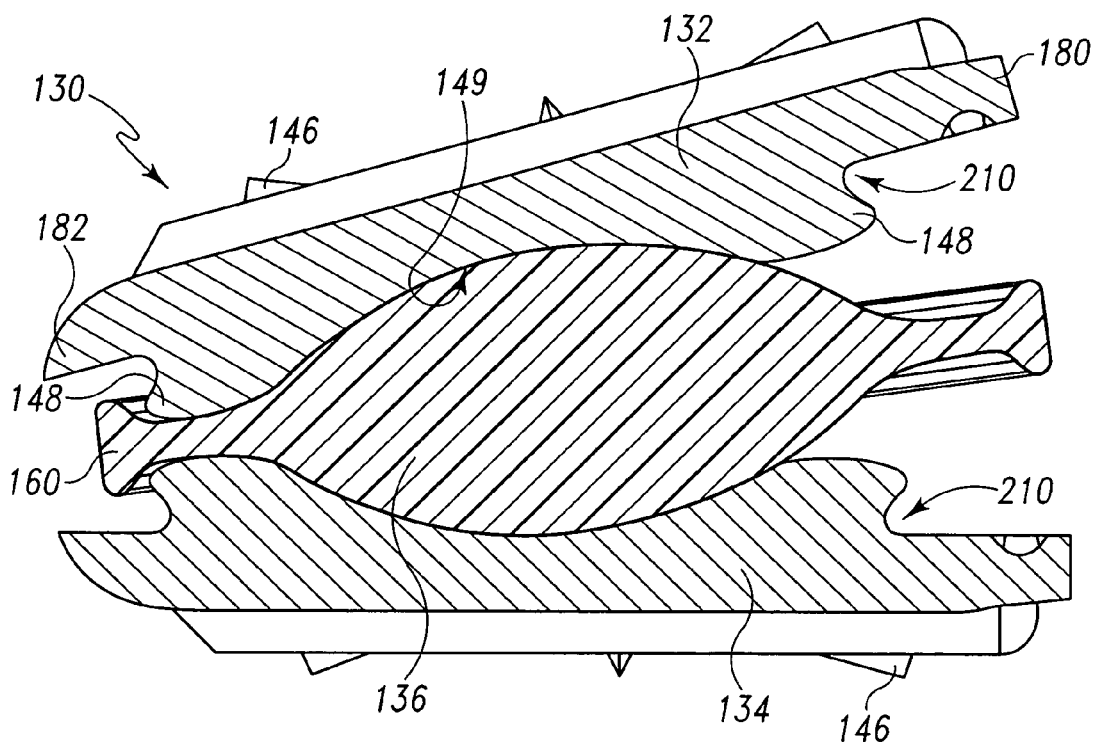
FIG. 9 shows a cross-sectional view of the intervertebral disc prosthesis through line XI-XI of FIG. 5.
Figure 12:
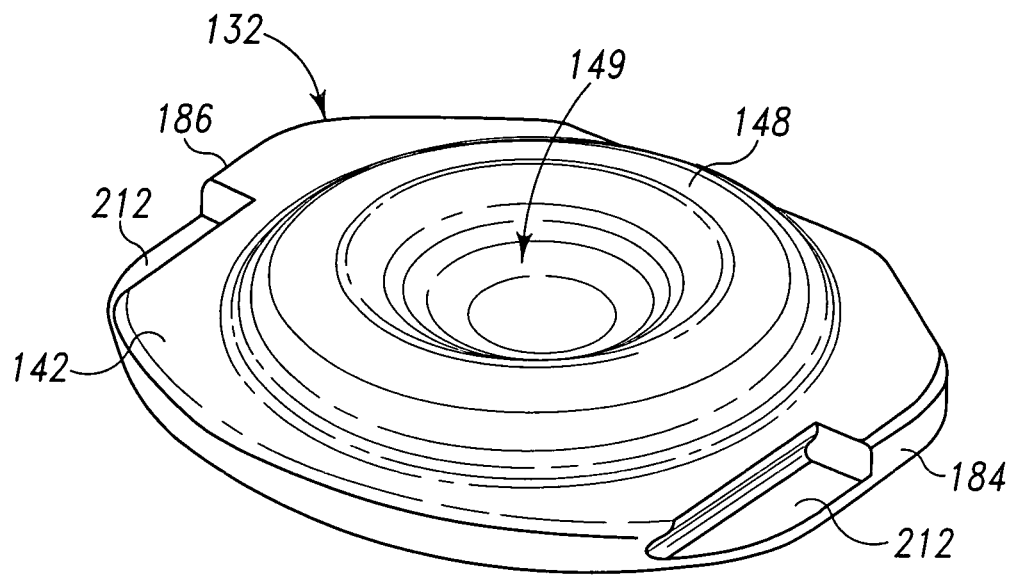
FIG. 12 shows a perspective view of an alternative embodiment of the bottom surface of an endplate of the intervertebral disc prosthesis of FIG. 4.

Another feature designed to assist with insertion of the prosthesis device are retention surfaces in the form of indentations positioned on the endplates, such as grooves, notches, cavities, channels, crevices, or other recesses. As best seen in FIGS. 4, 8 and 9, in one embodiment, the retention surfaces take the form of grooves 210 formed by the collar 148 of the endplate. The grooves 210 are dimensioned to receive and engage prongs or "retaining arms" of the disc insertion tool, allowing the endplate to be retained by the instrument during insertion, as explained in further detail below. Preferably, the indentations are designed to allow the insertion/distraction instrument to hold the endplates and core of the prosthesis simultaneously to facilitate insertion of the prosthesis as a unitary assembled piece. In an alternative embodiment, such as that shown in FIG. 12, the indentations take the form of notches 212 in the anterior corners on the left side 184 and right side 186 of the endplate 132. In this embodiment, the prongs of the insertion/distraction instrument grasp the surface of the endplate exposed by the notches 212 in order to hold the endplate and encourage the endplate toward the intervertebral space.

Another feature of the intervertebral prosthesis 130 are lateral holding features, such as notches, holes, grooves, indentations, protrusions or other structural features that provide an easy means of grasping the endplates or the intervertebral prosthesis 130 in general. Examples of lateral holding features include the hole 220 in the central channel of FIG. 13 and the notches 212 in the lower surface 142 of plate 132 in FIG. 12. These lateral holding features facilitate non-anterior insertion of the intervertebral prosthesis 130 and non-anterior revision/retrieval of the prosthesis. In particular, the lateral holding features provide structural components that may be easily grasped by instrumentation that may be used to properly orient the prosthesis 130 during implantation or help retract an implanted prosthesis. Alternatively, the groove 210 formed in the collar 148 of the endplate could be a circumferential groove, such that an instrument could attach to this groove from any direction, including anterior, lateral, or posterior surgical approaches. An example of an embodiment with the circumferential groove is shown in FIG. 12A.

Figure 12A:
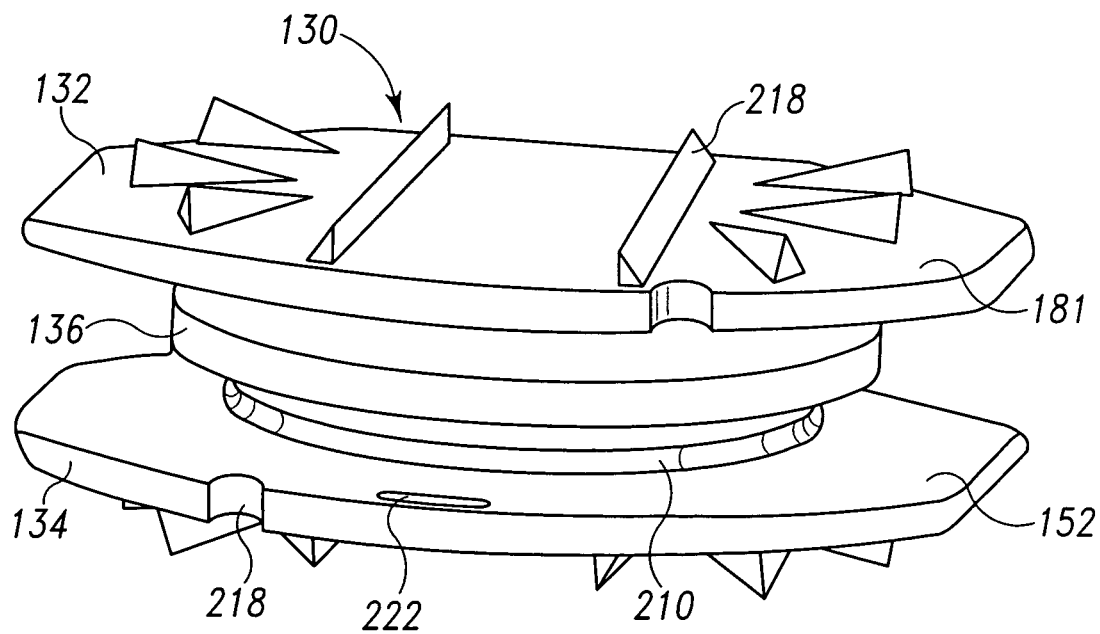
FIG. 12A shows a perspective view of an alternative embodiment of the intervertebral disc prosthesis of FIG. 4 including additional insertion features.

With reference to FIG. 12A, an alternative embodiment of the intervertebral disc prosthesis 130 includes additional insertion features. In particular, an anti-rotation notch 218 is provided in both the superior plate 132 and the inferior plate 134. The anti-rotation notch 218 takes the form of a semi-cylindrical notch carved in the anterior edge 181 of the endplate, extending from the upper surface of the endplate to the lower surface of the endplate. As explained in further detail below, the anti-rotation notch is designed to engage a peg on the disc insertion tool, and prevent rotation of the disc 130 during the insertion process.

As also shown in FIG. 12A, the intervertebral disc prosthesis 130 may include a spring-arm detent 222 formed in each endplate 132, 134. The spring arm detent 222 is formed in the lower surface 142 of the superior plate 132 and the upper surface 152 of the inferior plate 134. Each spring arm detent 222 extends partially into the endplate and provides a small cavity designed to receive the lip of a spring arm on a disc insertion tool. As explained in further detail below, the interaction between the detent 222 and the spring arm of the disc insertion tool provides additional stability for the intervertebral disc prosthesis during the implantation process.

Shear-Limiting Features

With reference to FIGS. 8 and 9, the intervertebral disc prosthesis 130 is configured to allow the endplates 132 and 134 to rotate/pivot from front-to-back and side-to-side. FIG. 8 shows a cross-sectional view of the prosthesis 130 with the endplates 132 and 134 pivoting toward the left side. FIG. 9 shows a cross-sectional view of the prosthesis 130 with the endplates 132 and 134 pivoting to the posterior side 182. As shown in both FIG. 8 and FIG. 9, the degree to which the endplates are allowed to pivot is restricted by the radial flange 160 of the core 136. This restricted degree of pivot limits the amount of shear experienced by the endplates and core.

Figure 14A:
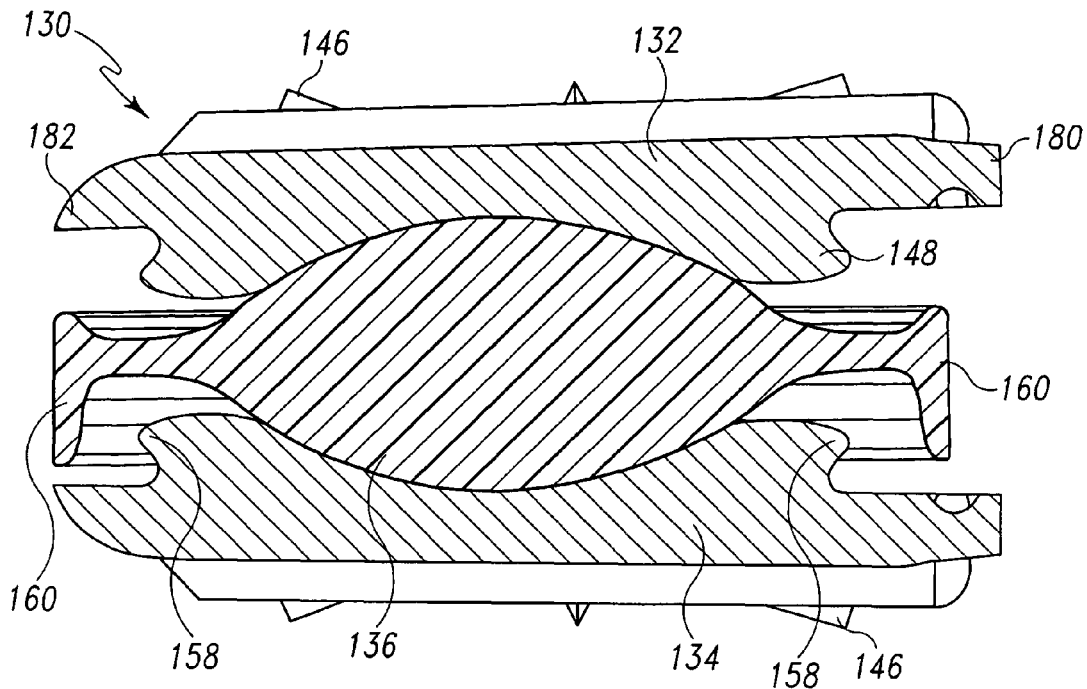
FIG. 14A shows a cross-sectional view of an alternative embodiment of the intervertebral disc prosthesis of FIG. 4 having a core with an extended flange configured to limit motion.

In an alternative embodiment, the radial flange 160 of the core may be extended toward the inferior endplate or the superior endplate to further limit or prevent articulation on that side of the core. For example, as shown in FIG. 14A, the flange 160 extends downward and encompasses the collar 158 of the inferior plate 134 in the neutral position (i.e., with the endplates and flange parallel), but does not contact the surface of the endplate 134 around the collar 158 in the neutral position. This configuration substantially limits the amount of pivoting allowed for the inferior endplate relative to the core. At the same time, the flange extends only slightly upward and does not encompass the collar 148 of the superior plate 132 in the neutral position. This allows normal pivoting of the superior endplate 132 relative to the core 136.

Figure 14B:
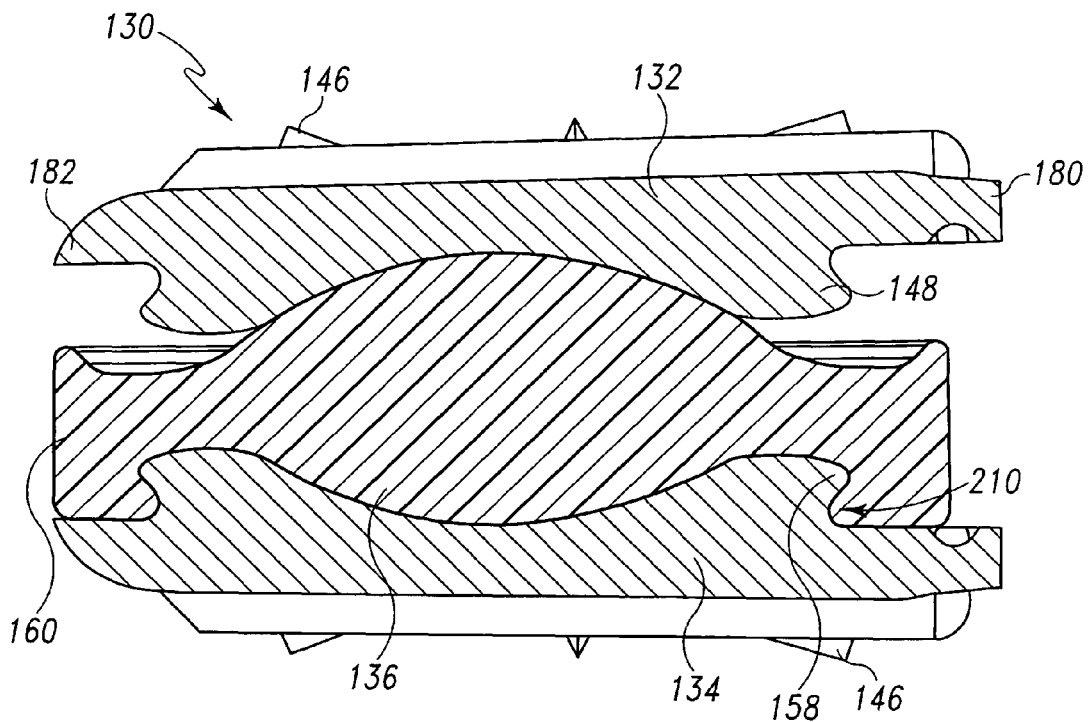
FIG. 14B shows a cross-sectional view of an alternative embodiment of the intervertebral disc prosthesis of FIG. 14A.

In another embodiment, such as that shown in FIG. 14B, the core 136 and flange 160 are configured to extend to the inferior endplate 134 and encase the collar 158 of the inferior endplate. In this embodiment, the core includes a lower surface area that substantially conforms to and engages an upper surface area of the inferior endplate. In an alternative embodiment, this lower surface area of the core could engage the groove 210 in the collar 158, such as with a snap fit. When securing the core to the inferior endplate, the core may be stretched and pressed to properly engage the lower surface of the core with the upper surface of the inferior endplate, thus properly positioning the core on the inferior endplate 134. After positioning the core 136 on the inferior endplate 134, the extended flange on the core prevents the inferior endplate 134 from lateral bending and flexion relative to the core 136. Accordingly, this configuration provides a shear limiting feature for the prosthesis.

In yet another embodiment, the flange 160 extends to the surface of the inferior endplate and includes protrusions that are press-fit into holes or other indentations formed in the surface of the inferior endplate 134. In this embodiment, the core 136 is fixed to the inferior plate by the protrusions that fit into the holes, preventing movement of the endplate 134 relative to the core 136. These protrusions on the core may be press-fit into the holes in the inferior plate when the physician assembles the prosthesis. Accordingly, this configuration also provides a shear limiting feature for the prosthesis.

Each of the above embodiments are designed to limit the amount of articulation between the endplates 132 and 134 and the core 136 and thus provide shear resistance to help protect the facets. Although the features have been shown with respect to the inferior endplate 134, they could likewise be provided with respect to the superior endplate 132.

Alternative Materials

As discussed above, the metal endplates 132, 134 may be comprised of a cobalt chromium alloy. The core 136 may be comprised of a plastic material such as ultra high molecular weight polyethylene. Because plastic materials are typically not radio-opaque, a cobalt chromium alloy wire may be provided around the core to allow the physician to determine the location of the core when viewing an x-ray image of an installed prosthesis. The cobalt chromium alloy wire is typically inserted into a channel on the core, such as channel 37 of FIG. 1 and channel 137 of FIG. 4.

In many cases, a physician may desire an MRI image rather than an x-ray image of an implanted prosthesis. Unfortunately, cobalt chromium alloy is not MRI compatible. Thus, in an alternative embodiment of the prosthesis, the endplates 132 and 134, and the wire in the core channel 137, are all comprised of titanium. The use of titanium allows the endplates and core wire of an implanted prosthesis to be MRI compatible. Other MRI compatible materials that could be used for the endplates and core wire include ceramics, polycarbonate-polyurethane (PCPU), polyetheretherketone (PEEK), or composites thereof.

In addition to alternative materials that make the intervertebral prosthesis MRI compatible, other materials may be advantageous to the surgeon, depending upon the desired outcome for the patient. For example, a ceramic core could be used for excellent wear performance in the youngest patients. A PCPU core could be used to offer shock-absorbing capabilities for more active patients.

Composite Core

Figure 15:
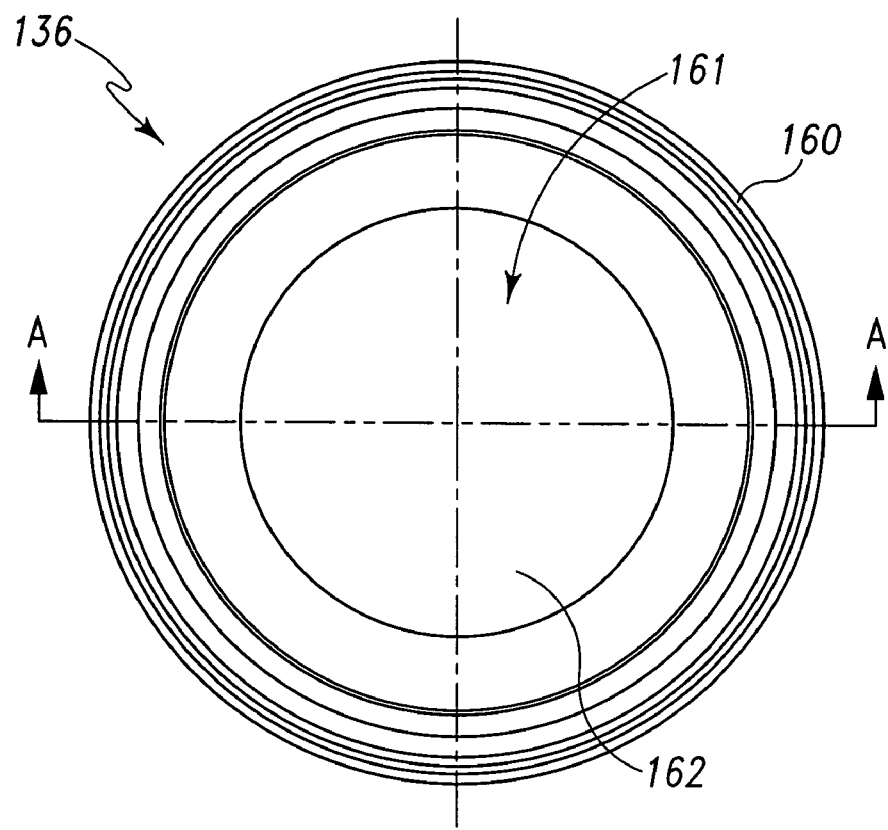
FIG. 15 shows a top view of an alternative embodiment of a core of the intervertebral disc prosthesis of FIG. 4.
Figure 16:
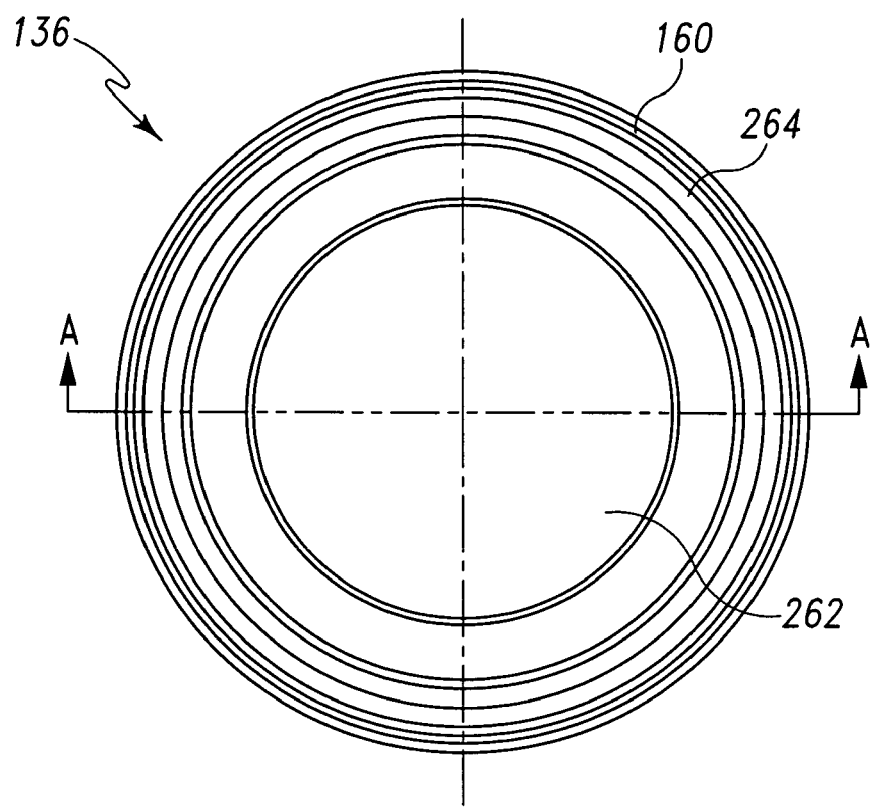
FIG. 16 shows a top view of another alternative embodiment of a core of the intervertebral disc prosthesis of FIG. 4.
Figure 17:
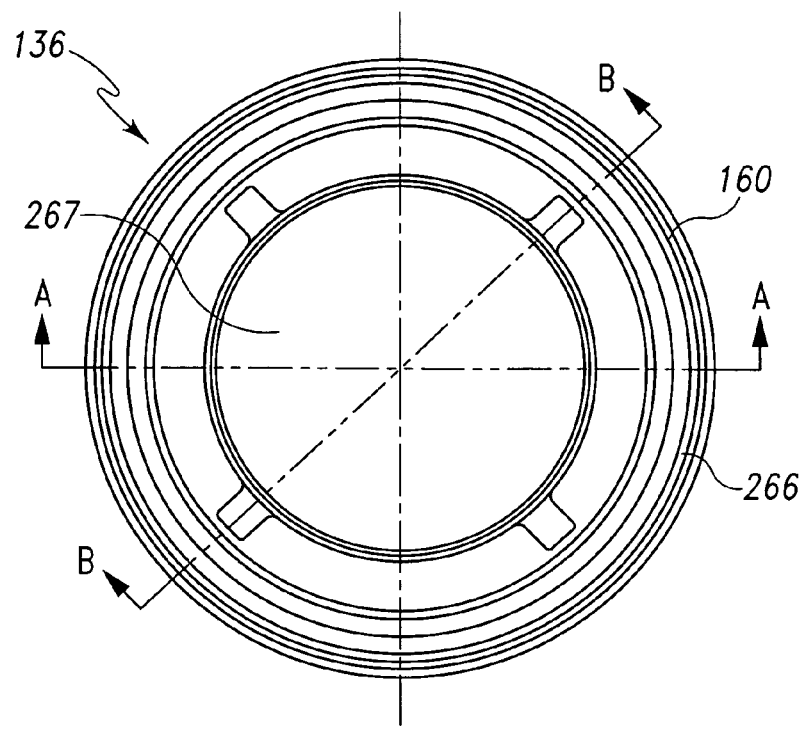
FIG. 17 shows a top view of yet another alternative embodiment of a core of the intervertebral disc prosthesis of FIG. 4.

In one embodiment, the core 136 is a composite core comprised of a plurality of different portions made of different materials exhibiting different properties. For example, FIGS. 15-17 show a plurality of different embodiments for a composite core comprising at least two materials with different properties, joined to form a single component. One embodiment of the composite core is a dual durometer core having a relatively soft bearing surface and a hardened flange.

Figure 15A:
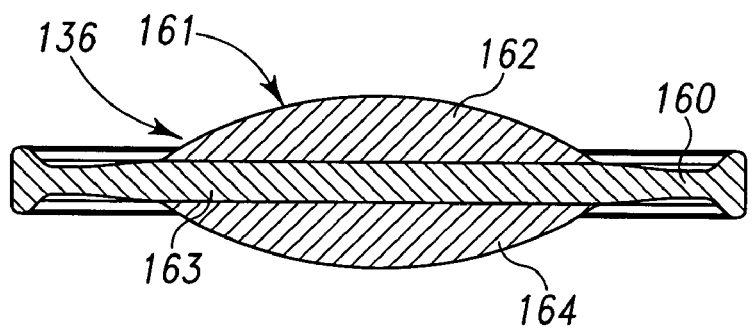
FIG. 15A shows a cross-sectional view of the core of FIG. 15 through line A-A.

With reference to FIGS. 15 and 15A, the core 136 is formed as a three-part composite core comprising a central disc portion 163, an upper bearing portion 162, and a lower bearing portion 164. The radial flange 160 is provided by the disc portion 163 and encompasses a convex bearing surface 161. The bearing surface 161 is provided by the upper bearing portion 162 and the lower bearing portion 164. The surface of the upper bearing portion 162 is designed to engage the socket 149 of the superior endplate 132 and the surface of the lower bearing portion 164 is designed to engage the socket of the inferior endplate 134. The upper bearing portion 162 and lower bearing portion 164 are fixed to the disc portion 163 such that the core is provided as a unitary piece. The core 136 may be configured such that the bearing portions 162, 164 attach to the disc portion 163 by any number of different methods, such as press-fit, threaded engagement, snap fit, welding, insert or two-shot injection molding, insert compression molding, brazing, bonding with adhesives, sintering, or other methods as will be recognized by those of skill in the art.

Figure 16A:
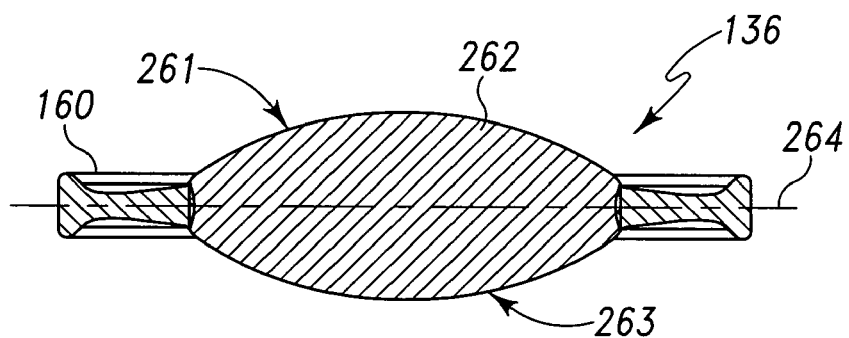
FIG. 16A shows a cross-sectional view of the core of FIG. 16 through line A-A.

Another embodiment of a composite core is shown in FIGS. 16 and 16A. In this embodiment, the core 136 is a two-part composite core comprising a central bearing portion 262 and an outer ring portion 264 encircling the central bearing portion. The top surface 261 of the central bearing portion 262 is designed to engage the socket of the superior plate 132, and the bottom surface 263 of the central bearing portion 262 is designed to engage the socket of the inferior plate 134. The outer ring portion 264 is the flange 160 of the core 136. When the central bearing portion 262 is comprised of a relatively soft material and the outer ring portion 263 is comprised of a relatively hard material, the ring portion 263 acts as a retaining wall for the bearing portion 262, making the bearing portion creep resistant. In particular, when the soft material of the bearing portion 262 is compressed following implantation in the patient, the harder material of the ring portion 263 prevents the soft material of the bearing portion from deforming into a flatter shape. Alternatively, the bearing portion 262 may be comprised of a relatively hard wear-resistant material while the ring portion 263 may be comprised of a relatively resilient or tough material that limits extreme motions, such as that shown in FIGS. 14 and 14A. The core 136 may be configured such that the bearing portion 262 is attached to the ring portion 163 by any number of different methods, such as press-fit, snap fit, welding, insert or two-shot injection molding, insert compression molding, brazing, bonding with adhesives, sintering, or other methods as will be recognized by those of skill in the art.

Figure 17A:
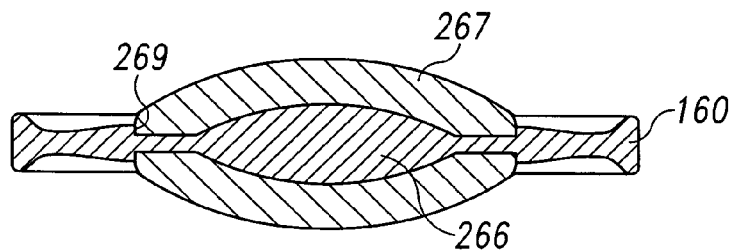
FIG. 17A shows a cross-sectional view of the core of FIG. 17 through line A-A.
Figure 17B:
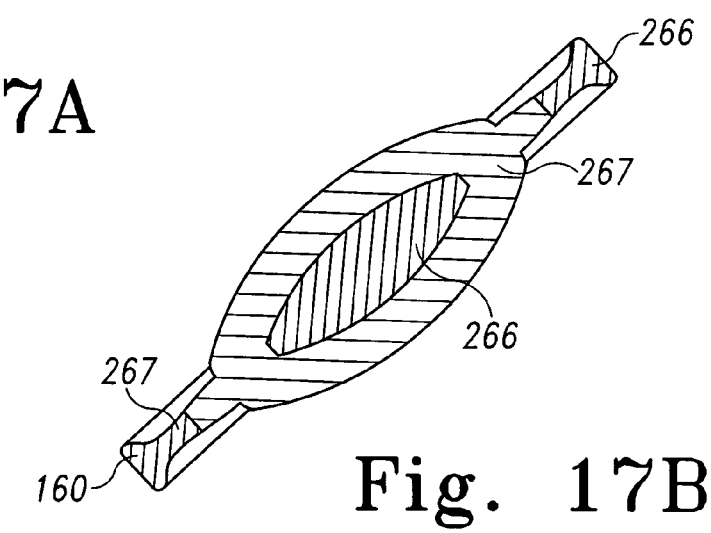
FIG. 17B shows a cross-sectional view of the core of FIG. 17 through line B-B.

FIGS. 17, 17A and 17B show yet another embodiment of the prosthesis core 136. In this embodiment, the prosthesis core 136 is specifically designed to allow injection molding of two materials using insert or two-shot molding, where a second material is molded over a first material. As shown in FIG. 17A, the core comprises an inner skeleton 266 of a first material and an outer bearing flesh 267 of a second material. The skeleton 266 is generally disc shaped and the material of the skeleton extends continuously across the core from one point on the flange 160 to an opposite point on the flange. The skeleton also provides a ridge 269 where the bearing flesh 267 abuts the skeleton 266. However, in certain locations on the core 136, as shown in FIG. 17B, the skeleton does not extend continuously across the core, and is interrupted by portions of bearing flesh 267. This arrangement provides a cohesive part with strong mechanical interconnections. Furthermore, if the bearing flesh 267 is comprised of a relatively soft material and the skeleton 266 is comprised of a relatively hard material, the flange of the skeleton provides a retaining wall along with the ridge 269 to prevent creep of the soft bearing material during compression. As discussed above, the arrangement shown in FIGS. 17-17B is specifically configured for insert molding of the core.

From the above examples it will be clear that a core 136 may be provided in multiple portions comprised of differing materials such that the properties of the core vary from location to location in an advantageous manner. For example, as discussed above, the core may be manufactured in a manner such that the core provides a soft bearing surface on the exterior and a rigid support skeleton on the inside. As another example, the core may be manufactured with a hard bearing surface and a relatively resilient skeleton.

Example materials for use with the core include PEEK or titanium with a wear-improving coating, PCPU, MMC, cobalt chromium alloy, ceramics, double-network hydrogels, in addition to ultra-high molecular weight polyethylene (UHMWPE). Alternate combinations of interest from a wear perspective include metal matrix composites (MMC) with cobalt chromium or MMC with ceramic. Example ceramics include synthetic ruby, zirconia, alumina, zirconia toughened alumina (ZTA), Y-TZP, silicon nitride, or combinations thereof.

Examples of core material combinations and arrangements include a ruby bearing portion brazed to a metal flange; a cobalt chromium, titanium or stainless steel flange press fit around a ceramic bearing; a MMC such as titanium with titanium carbide bearing surface over a titanium skeleton; polycarbonate-polyurethane (PCPU) or UHMWPE bearing surfaces injection or compression molded over a metal flange insert; a ceramic bearing with a PCPU or UHMWPE flange; or a PEEK bearing with PCPU or a metal flange skeleton. As another example, a PCPU core could be produced by multi-shot or insert injection molding a relatively rigid central frame and flange with a relatively soft outer bearing surface (e.g., shore 55D frame and shore 80A bearing). In another example embodiment, layered sintering of MMC to a similar metal results in a MMC bearing surface applied to a metal frame, thus providing a bearing surface with ceramic-like properties and a retention flange with non-ceramic (i.e., non-brittle) properties.

Modular Prosthesis Components

As described above, various configurations and compositions are possible for the endplates 132, 134 and core 136. With a wide variety of differing endplates and cores available, the surgeon may desire a specific endplate and core combination based on the particular needs of a patient. Therefore, the various endplates and cores are made available to the surgeon as part of a modular prosthesis system, where differing endplates may be matched with any number of different cores to arrive at the desired prosthesis. This provides the surgeon with a method of designing an intervertebral prosthesis that is customized to the needs of the particular patient.

When customizing the intervertebral prosthesis, the surgeon analyzes and/or tests the patient to determine features that may be desirable for the patient based on his or her particular situation. These features may include, for example, material composition of the prosthesis, structural features, and size of the prosthesis. The surgeon then decides which features to include in the patient's intervertebral prosthesis, and places an order for the desired prosthesis with the prosthesis manufacturer. The surgeon's decision to order certain structural features, sizes, or materials for the prosthesis will likely be made based on the patient's concerns, the patient's medical history, testing conducted on the patient, the patient's age, the patient's size, the patient's health, the patient's activity level, and the physician's general best judgment. After the customized prosthesis is ordered, the manufacturer puts together a prosthesis package for the physician and patient by selecting the modular endplate and core components that provide the desired prosthetic device. The components are then delivered to the physician for implantation in the patient.

As an example of the modular prosthesis system in operation, consider a particular situation where the patient is allergic to nickel. In this situation, the surgeon will not want to use a cobalt chromium endplate, since nickel is found in cobalt chromium alloy, and the patient's body is likely to have an adverse reaction to the nickel. However, because the prosthesis described herein may be assembled from various modular components, the surgeon will have the choice of selecting an endplate that contains no nickel, such as a titanium endplate. In addition, the surgeon may determine that a patient may benefit from a core having a rigid ceramic-like bearing surface with a non-brittle and more cushioned retention flange. For this core, the surgeon may use a core comprised of an MMC material applied to a metal frame using layered sintering. As another example, the surgeon may decide that movement of the inferior endplate should be restricted for a particular patient. In this case, the surgeon may order a prosthesis having a core similar to that of FIG. 14B as opposed to the core shown in FIGS. 8 and 9. In any case, the modular characteristics of the prosthesis system described herein allow the surgeon to choose endplates and a core that together provide the prosthesis that is most appropriate for the patient.

After receiving an order for an intervertebral disc prosthesis having a specified superior plate, core, and inferior plate, the seller of the prosthetic devices obtains the appropriate modular components and sends them to the physician. After receiving the modular components, the physician assembles the components before implanting the assembled prosthesis in the patient.

Insertion of Intervertebral Prosthesis

After selecting and receiving the proper endplates 132 and 134 and core 136 for a particular patient, the surgeon assembles the intervertebral prosthesis 130 by sandwiching the core between the endplates. Once assembled the prosthesis may be implanted in the patient as a complete unit using an insertion/distraction instrument.

Figure 18:
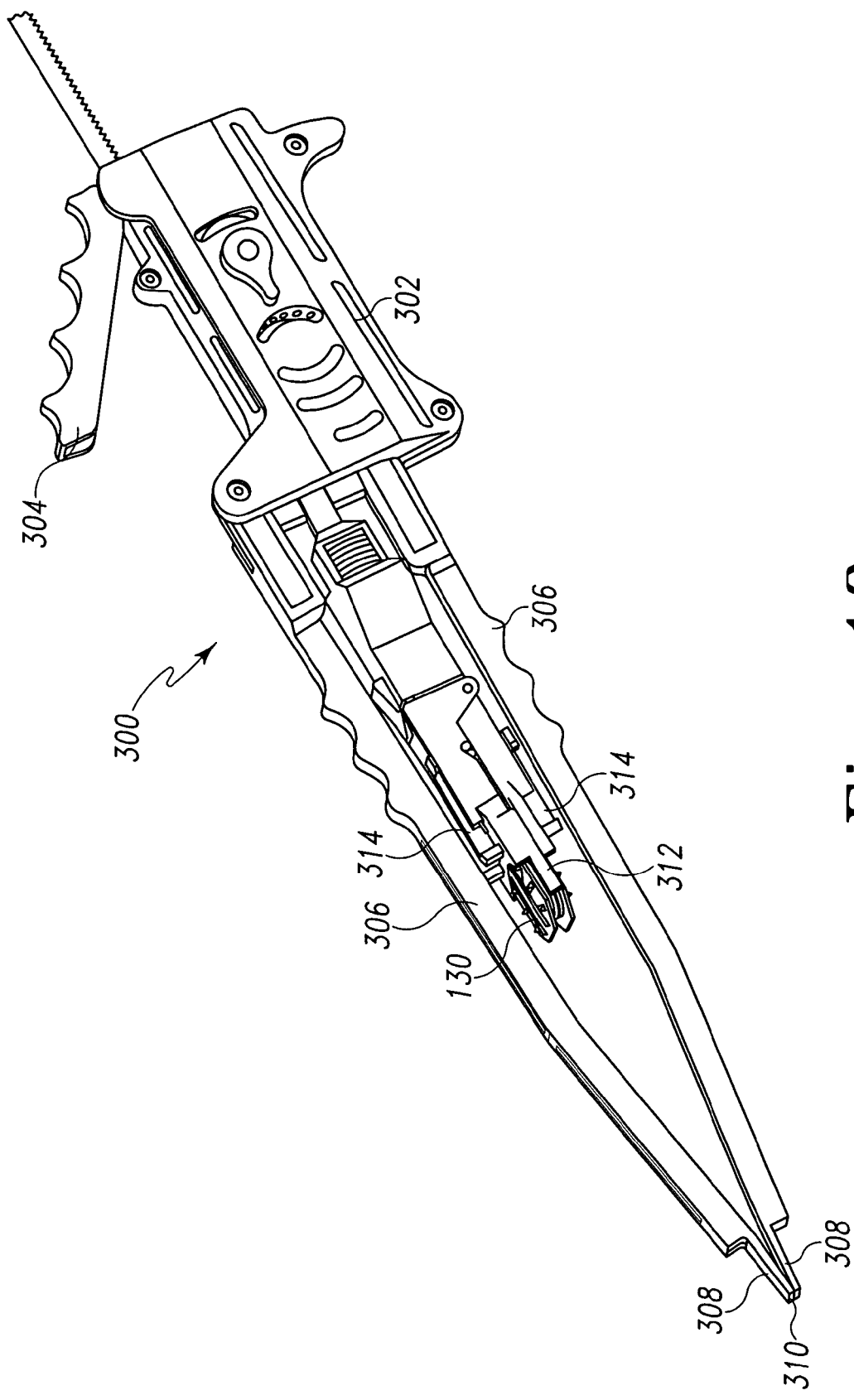
FIG. 18 shows a perspective view of an disc insertion tool for the intervertebral disc prosthesis of FIG. 4 in a retracted position.

In particular, with reference to FIG. 18 an intervertebral prosthesis 130 is shown positioned within a disc insertion tool 300. The disc insertion tool 300 generally includes a handle 302 and associated lever 304. Separate insertion arms 306 extend from the handle. The insertion arms 306 end in flat fingers 308 that contact one another at a tip 310 opposite the handle 302. Holding prongs/retention arms 312 are provided between the insertion arms. The retention arms 312 are designed to retain the prosthesis 130 on the disc insertion tool 300 by engaging the insertion features, such as indentations 210, 212 positioned on the endplates 132 and 134, as discussed above. Activation of the lever 304 causes a ratcheting operation that moves the insertion arms 312 and prosthesis 300 toward the tip 310.

Figure 19:
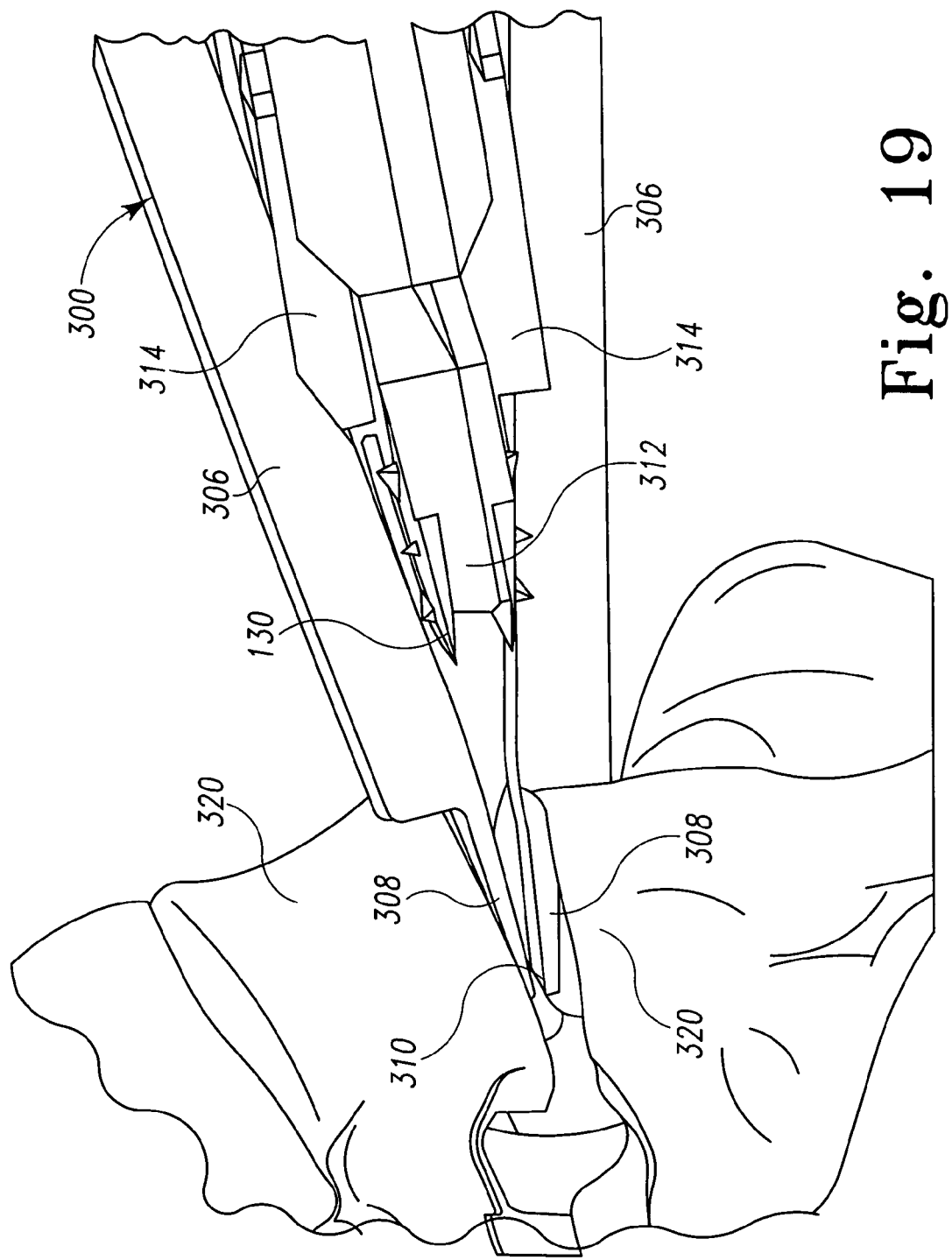
FIG. 19 shows a perspective view of the disc insertion tool of FIG. 18 inserting the intervertebral disc prosthesis between vertebral bodies.

As shown in FIG. 19, once the old disc is removed from the intervertebral space, the tip 310 of the disc insertion tool is placed in the intervertebral space with blunt edges of the insertion arms 306 positioned against the vertebral bodies 320. As the prosthesis is gradually ratcheted toward the intervertebral space the central channel 202 of the prosthesis 130 receives the insertion arms/distracting ramp 306, and this engagement properly orients and stabilizes the prosthesis 130 as it enters the vertebral space. Furthermore, as the prosthesis is ratcheted further and further down the insertion arms 306 toward the tip 310, the prosthesis causes the insertion arms 306 to spread apart near the tip 310. As the insertion arms 306 and fingers 308 are moved apart, space is created between the vertebral bodies 320 for the prosthesis 130.

The height of the fingers 308 in the intervertebral space is greater than the height of the teeth 146 on the prosthesis 130. This allows the prosthesis 130 to slide into position between the vertebral bodies 320, moving along the insertion arms 306 and fingers 308 without contacting the vertebral bodies 320 until the fingers 308 are removed from the intervertebral space.

Figure 20:
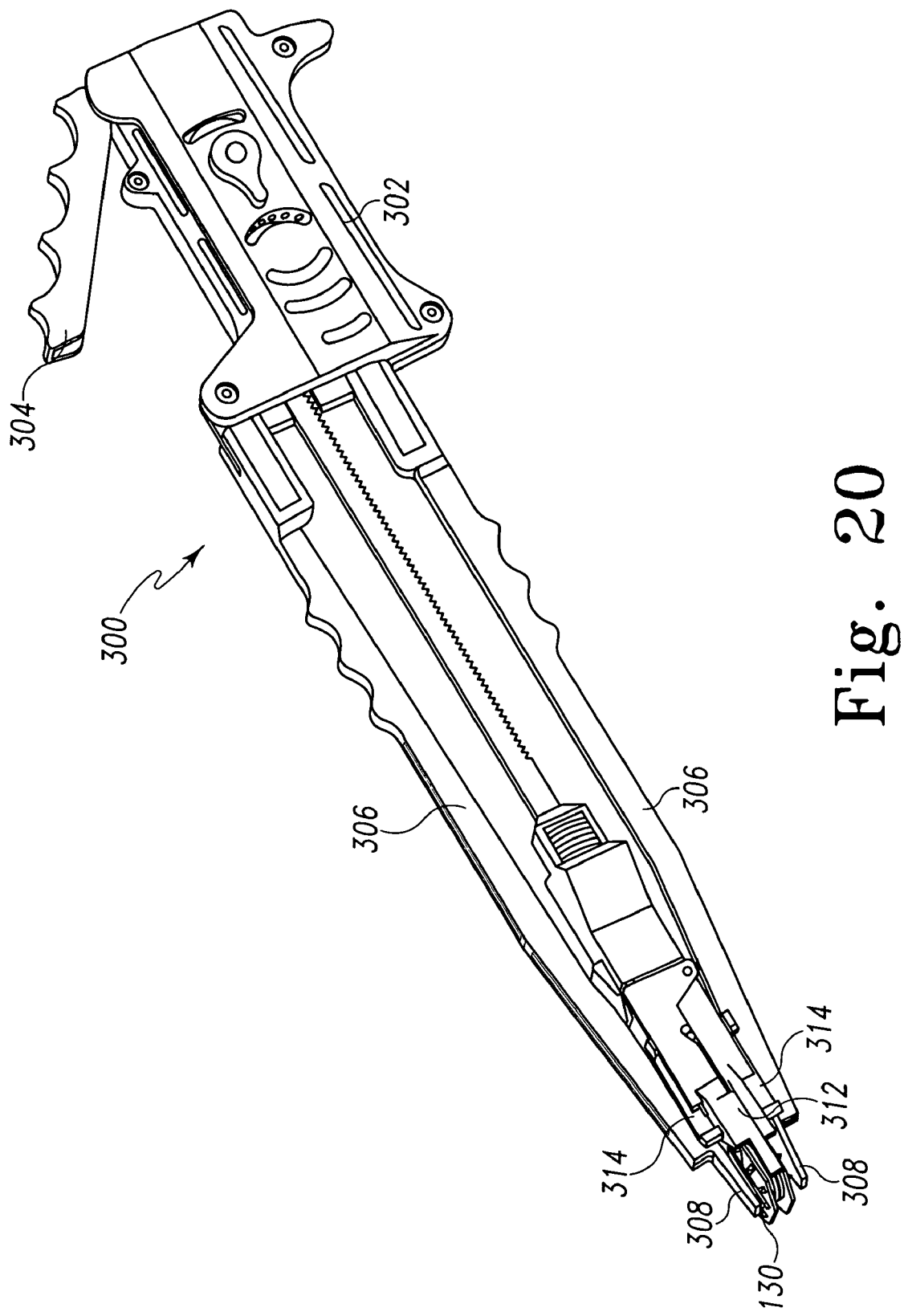
FIG. 20 shows a perspective view of the disc insertion tool of FIG. 18 in an extended position.

Stop blocks 314 are provided on the disc insertion tool toward the rear of the retention arms 312. In one embodiment, the position of the stop blocks 314 could be adjustable relative to the insertion arms 312. The stop blocks 314 are designed to prevent the prosthesis 130 from being inserted too far into the intervertebral space. In particular, when the prosthesis 130 has been moved down the insertion arms and to a position in the intervertebral space such that the disc insertion tool should be removed, the stop blocks 314 will contact the vertebral bodies 320 at the end of the insertion arms 306. FIG. 20 shows the disc insertion tool 300 near such a position. Continued ratcheting of the lever 304 at this point causes the insertion arms 306 to retract from the vertebral bodies 320, as the stop blocks 314 press against the vertebral bodies. Once the insertion fingers 308 are removed from the intervertebral space, the teeth 146 of the prosthesis 130 contact the vertebral bodies 320. Natural compression of the prosthesis 130 by the vertebral bodies 320 causes the teeth 146 to sink into the vertebral bodies, securing the prosthesis 130 in place between the vertebral bodies. Bony in-growth between the endplate and bone further secures the prosthesis in place over time.

Figure 21:
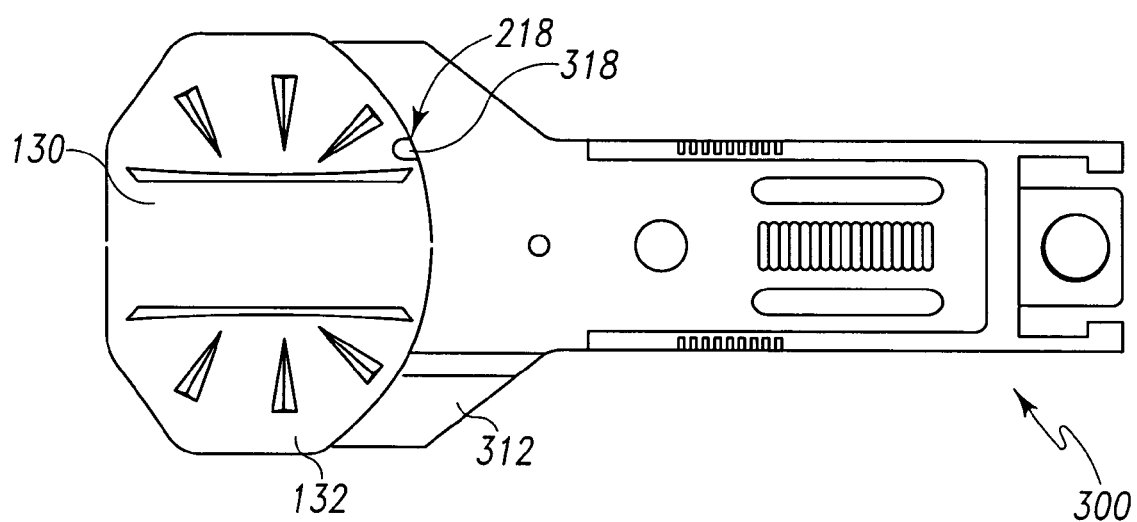
FIG. 21 shows a top view of the intervertebral disc prosthesis of FIG. 12A engaged with a disc insertion tool.
Figure 22:
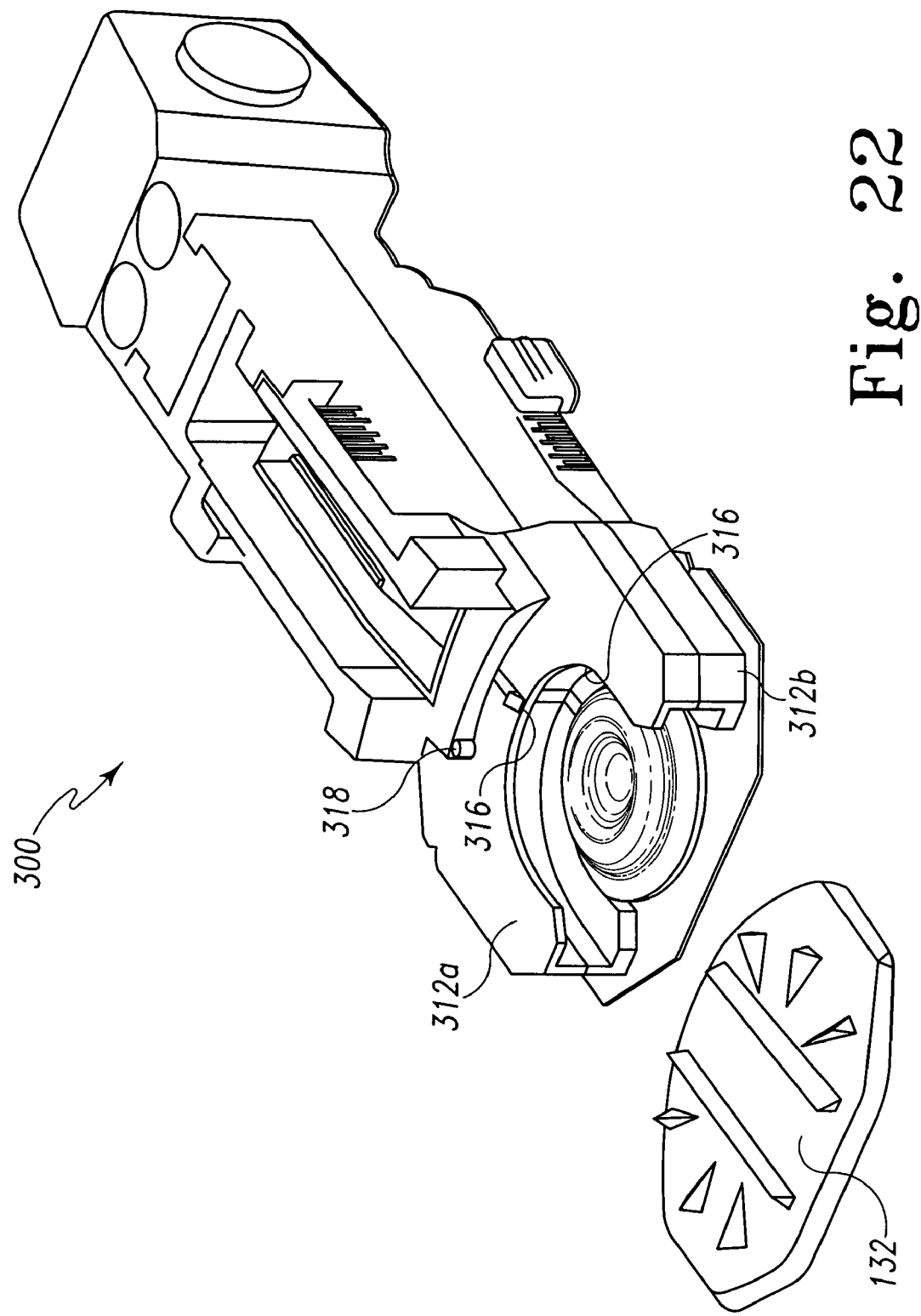
FIG. 22 shows a perspective view of the disc insertion tool of FIG. 21.

An alternative embodiment of disc insertion tool 300 is shown in FIGS. 21 and 22. This embodiment of the disc insertion tool 300 is configured for use with the intervertebral disc prosthesis shown in FIG. 12A. In this embodiment, the disc insertion tool 300 includes anti-rotation pegs 318 as well as spring arms 316. The anti-rotation pegs 318 are fixed to the retention arms 312 of the disc insertion tool 300. One anti-rotation peg 318 is provided on a top retention arm 312a and another anti-rotation peg is provided on a lower retention arm 312b (the lower anti-rotation peg is not shown in the figures). When the anti-rotation pegs 318 are fully inserted into the anti-rotation notches 218 of the disc prosthesis 130, as shown in FIG. 21, the prosthesis 130 is prevented from rotating relative to the disc insertion tool, thus maintaining the proper orientation of the disc prosthesis during the implantation procedure.

The spring arms 316 are provided at the central back portion of the retention arms 312. The spring arms 316 are cantilever arms having resilient qualities that allow the spring arms to bend and spring back into place. The spring arms 316 each include a lip extending from the end of the spring arm. These lips are designed to fit into the spring arm detents 222 of the disc prosthesis 130 (see FIG. 12A). When the lips of the spring arms 316 extend into the spring arm detents 222, the disc prosthesis 130 is further secured to the insertion tool 300 during the implantation process. Once the disc prosthesis 130 is properly situated in the intervertebral space, the spring arms 316 may be automatically released, allowing the lips of the spring arms to move away from the spring arm detents 222. With the spring arms 316 released, the disc insertion tool 300 may be pulled away, leaving the disc prosthesis 130 in place in the intervertebral space.

Although the present invention has been described with respect to certain preferred embodiments, it will be appreciated by those of skill in the art that other implementations and adaptations are possible. For example, the prosthetic disc components shown in the attached drawings are most commonly associated with artificial lumbar discs, but the features described herein could also apply to other discs such as artificial cervical discs. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intervertebral disc prosthesis comprising:
   a) a first prosthesis component including a vertebra facing surface;
   b) a second prosthesis component including a vertebra facing surface; and
   c) a composite core positioned between the first prosthesis component and the second prosthesis component, wherein the composite core includes a first portion comprised of a first material and a second portion comprised of a second material, wherein the first material has properties differing from the second material,
      wherein, when said intervertebral disc prosthesis is viewed in a cross-sectional view, said first portion defines a continuous loop forming (i) a first bearing surface configured to contact said first prosthesis component, and (ii) a second bearing surface configured to contact said second prosthesis component, and
      wherein said second portion extends through said continuous loop.

2. The intervertebral disc prosthesis of claim 1 wherein the first prosthesis component comprises a first plate and the second prosthesis component comprises a second plate.

3. The intervertebral disc prosthesis of claim 2 wherein the first plate includes a first socket that defines a first substantially spherical surface.

4. The intervertebral disc prosthesis of claim 2 wherein the second plate includes a second socket that defines a second substantially spherical surface.

5. The intervertebral disc prosthesis of claim 2 wherein an upper surface of the core is substantially spherical.

6. The intervertebral disc prosthesis of claim 2 wherein a lower surface of the core is substantially spherical.

7. The intervertebral disc prosthesis of claim 1 wherein the second portion is a flange portion.

8. The intervertebral disc prosthesis of claim 7 wherein the flange portion is disc-shaped.

9. The intervertebral disc prosthesis of claim 1 wherein the first portion is injection molded.

10. The intervertebral disc prosthesis of claim 1 wherein the first portion is molded onto the second portion.

11. The intervertebral disc prosthesis of claim 1 wherein the first portion is fastened to the second portion.

12. The intervertebral disc prosthesis of claim 11 wherein the first portion is press-fit onto the second portion.

13. The intervertebral disc prosthesis of claim 1 wherein the first portion is comprised of a relatively soft material compared to the second portion.

14. The intervertebral disc prosthesis of claim 1 wherein the first material is a metal.

15. The intervertebral disc prosthesis of claim 1 wherein the first material is a polymer.

16. The intervertebral disc prosthesis of claim 1 wherein the first material is a ceramic.

17. The intervertebral disc prosthesis of claim 1 wherein the first material is a metal matrix composite.

18. An intervertebral disc prosthesis comprising:
    a) a first plate;
    b) a second plate; and
    c) a composite core positioned between the first plate and the second plate, the composite core comprising a superior bearing surface engaging the first plate, an inferior bearing surface engaging the second plate, and a radial flange encircling the superior bearing surface and the inferior bearing surface, wherein the superior bearing surface and the inferior bearing surface are comprised of a first material, and wherein the radial flange is comprised of a second material that is different from the first material,
       wherein, when said intervertebral disc prosthesis is viewed in a cross-sectional view, said first material defines a continuous loop forming (i) at least part of said superior bearing surface, and (ii) at least part of said inferior bearing surface, and
       wherein said second material extends through said continuous loop.

* * * * *